(12) United States Patent
Scheenstra et al.

(10) Patent No.: US 11,311,431 B2
(45) Date of Patent: Apr. 26, 2022

(54) ADJUSTER FOR USE WITH FLEXIBLE RESTRAINTS

(71) Applicant: Stryker Corporation, Kalamazoo, MI (US)

(72) Inventors: Levi Scheenstra, Plainwell, MI (US); Michael J. Hernandez, Portage, MI (US); Matthew Thomas Thielking, Schoolcraft, MI (US); Andrew J. Vandermoren, Vicksburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/125,073

(22) Filed: Dec. 17, 2020

(65) Prior Publication Data

US 2021/0100699 A1 Apr. 8, 2021

Related U.S. Application Data

(63) Continuation of application No. 16/281,729, filed on Feb. 21, 2019, now Pat. No. 10,918,540.

(51) Int. Cl.
*A61G 1/044* (2006.01)
*A44B 11/25* (2006.01)
*A61F 5/37* (2006.01)
*A44B 11/12* (2006.01)

(52) U.S. Cl.
CPC .......... *A61G 1/044* (2013.01); *A44B 11/2557* (2013.01); *A61F 5/3776* (2013.01); *A44B 11/125* (2013.01)

(58) Field of Classification Search
CPC ............... A44B 11/2557; A44B 11/125; Y10T 24/4016; Y10T 24/4084; Y10T 24/4072
See application file for complete search history.

(56) References Cited

U.S. PATENT DOCUMENTS

| 2,528,078 | A | 10/1950 | Quilter |
| 2,538,641 | A | 1/1951 | Elsner |
| 2,622,293 | A | 12/1952 | Wermlinger |
| 2,867,876 | A | 1/1959 | Elsner |
| 2,901,794 | A | 9/1959 | Prete, Jr. |
| 2,972,173 | A | 2/1961 | Weber |
| 2,981,993 | A | 5/1961 | Elsner |
| 2,998,626 | A | 9/1961 | Prete |
| 3,011,237 | A | 12/1961 | Prete, Jr. |
| 3,253,309 | A | 5/1966 | Baresch |
| 3,344,486 | A | 10/1967 | Eveland |

(Continued)

FOREIGN PATENT DOCUMENTS

| EP | 1623892 A1 | 2/2006 |
| JP | 2000104708 A | 4/2000 |

OTHER PUBLICATIONS

English language abstract and machine-assisted English translation for JP 2000-104708 extracted from espacenet.com database on Apr. 15, 2019, 10 pages.

*Primary Examiner* — Robert Sandy
(74) *Attorney, Agent, or Firm* — Howard & Howard Attorneys PLLC

(57) ABSTRACT

A harness system includes one or more harness assemblies. Each harness assembly includes a flexible restraint formed of a coated fabric. An adjuster is provided to adjust an effective length of the flexible restraint. The adjuster includes a frame, a restraint guide, and a cam.

20 Claims, 23 Drawing Sheets

(56) References Cited

U.S. PATENT DOCUMENTS

| | | | |
|---|---|---|---|
| 3,413,691 A | 12/1968 | Elsner | |
| 3,434,186 A | 3/1969 | Rennert | |
| 3,605,205 A | 9/1971 | Crissy | |
| 3,678,542 A | 7/1972 | Prete, Jr. | |
| 3,872,550 A | 3/1975 | Yang | |
| 3,898,715 A | 8/1975 | Balder | |
| 3,950,826 A | 4/1976 | Knoll et al. | |
| 4,464,811 A | 8/1984 | Holmes | |
| 4,660,889 A | 4/1987 | Anthony et al. | |
| 4,716,630 A | 1/1988 | Skyba | |
| 4,726,625 A | 2/1988 | Bougher | |
| 4,792,016 A | 12/1988 | Ingalsbe et al. | |
| 4,843,688 A | 7/1989 | Ikeda | |
| 4,881,303 A | 11/1989 | Martini | |
| 5,031,962 A | 7/1991 | Lee | |
| 5,039,169 A | 8/1991 | Bougher et al. | |
| 5,100,176 A * | 3/1992 | Ball | A44B 11/2557 24/171 |
| 5,160,186 A | 11/1992 | Lee | |
| 5,172,455 A | 12/1992 | Johnson et al. | |
| 5,979,982 A | 11/1999 | Nakagawa | |
| 6,343,841 B1 | 2/2002 | Gregg et al. | |
| 6,560,825 B2 | 5/2003 | Maciejczyk | |
| 6,868,585 B2 | 3/2005 | Anthony et al. | |
| 7,334,301 B2 | 2/2008 | Huang | |
| 7,343,650 B2 | 3/2008 | Baldwin et al. | |
| 7,404,239 B1 | 7/2008 | Walton et al. | |
| 7,444,720 B2 | 11/2008 | Huang | |
| 7,506,413 B2 | 3/2009 | Dingman et al. | |
| 8,087,696 B2 | 1/2012 | Mather et al. | |
| 8,820,788 B2 * | 9/2014 | Goudeau | A44B 11/2561 280/806 |
| 9,017,330 B2 | 4/2015 | Foerster et al. | |
| 9,102,301 B1 | 8/2015 | Baker et al. | |
| 9,254,778 B2 | 2/2016 | Gangakhedkar et al. | |
| 9,266,462 B2 | 2/2016 | Miller | |
| 9,332,810 B2 | 5/2016 | Hortnagl | |
| 9,387,791 B2 | 7/2016 | Mamie et al. | |
| 9,409,537 B2 | 8/2016 | Zhang et al. | |
| 9,433,258 B2 | 9/2016 | Hetrick et al. | |
| 9,622,547 B2 | 4/2017 | Seader | |
| 9,623,837 B2 * | 4/2017 | Moker | A44B 11/06 |
| 9,775,410 B2 | 10/2017 | Szewczyk et al. | |
| 9,980,537 B2 | 5/2018 | Aoyagi | |
| 10,080,693 B1 | 9/2018 | Scheenstra et al. | |
| 10,442,394 B2 * | 10/2019 | Hermann | B60R 22/1855 |
| 2006/0005293 A1 | 1/2006 | Frey et al. | |
| 2006/0102423 A1 | 5/2006 | Lang et al. | |
| 2008/0100051 A1 | 5/2008 | Bell et al. | |
| 2008/0168603 A1 | 7/2008 | Ayette et al. | |
| 2010/0043186 A1 | 2/2010 | Lesley | |
| 2010/0275420 A1 | 11/2010 | Huang | |
| 2012/0286501 A1 * | 11/2012 | Goudeau | A44B 11/2557 280/801.1 |
| 2015/0191114 A1 | 7/2015 | Blankenship | |
| 2015/0313778 A1 | 11/2015 | Chia et al. | |
| 2016/0338886 A1 | 11/2016 | Schroeder et al. | |
| 2018/0325717 A1 | 11/2018 | Dufek | |
| 2020/0268576 A1 | 8/2020 | Scheenstra et al. | |

\* cited by examiner

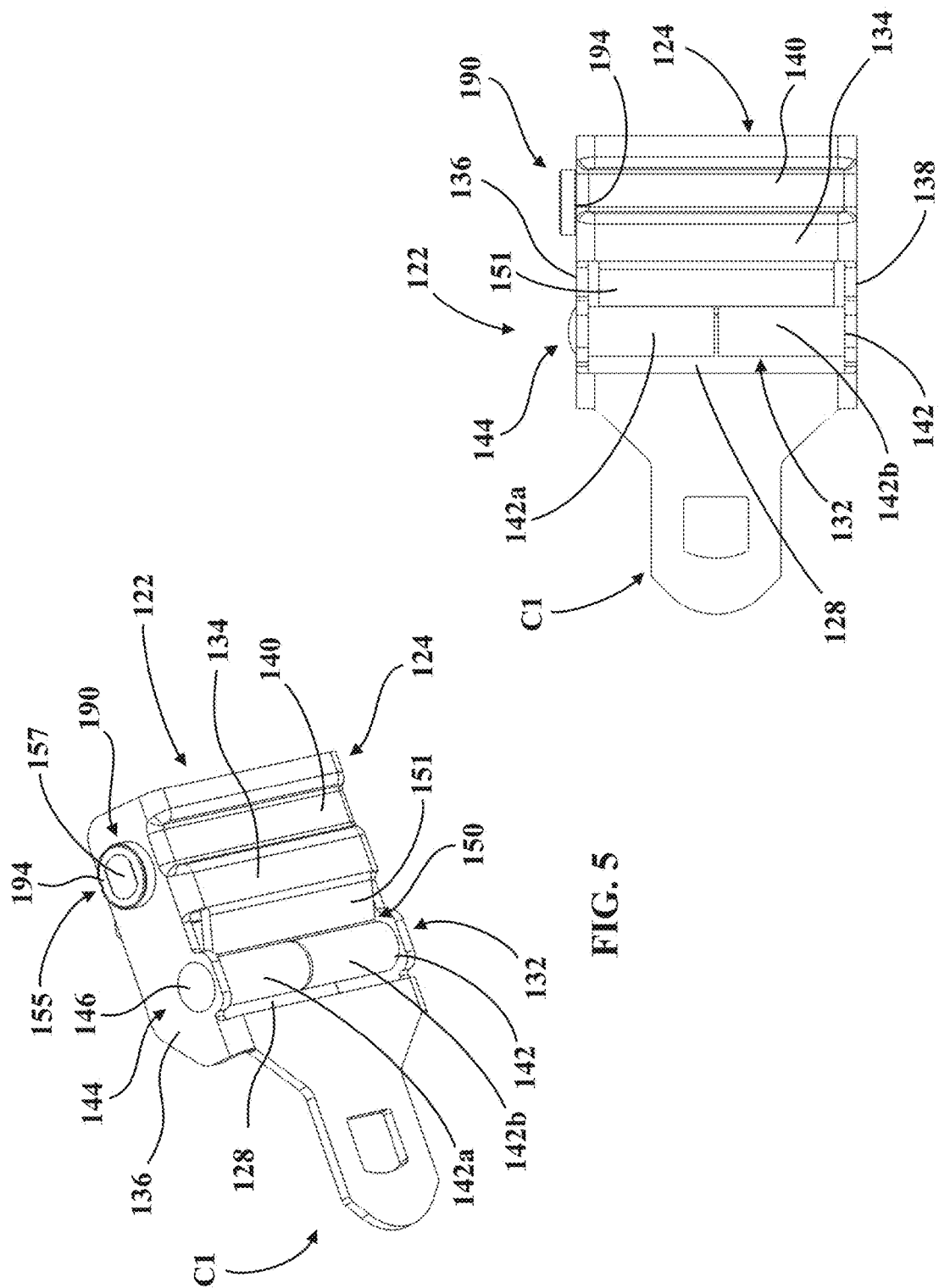

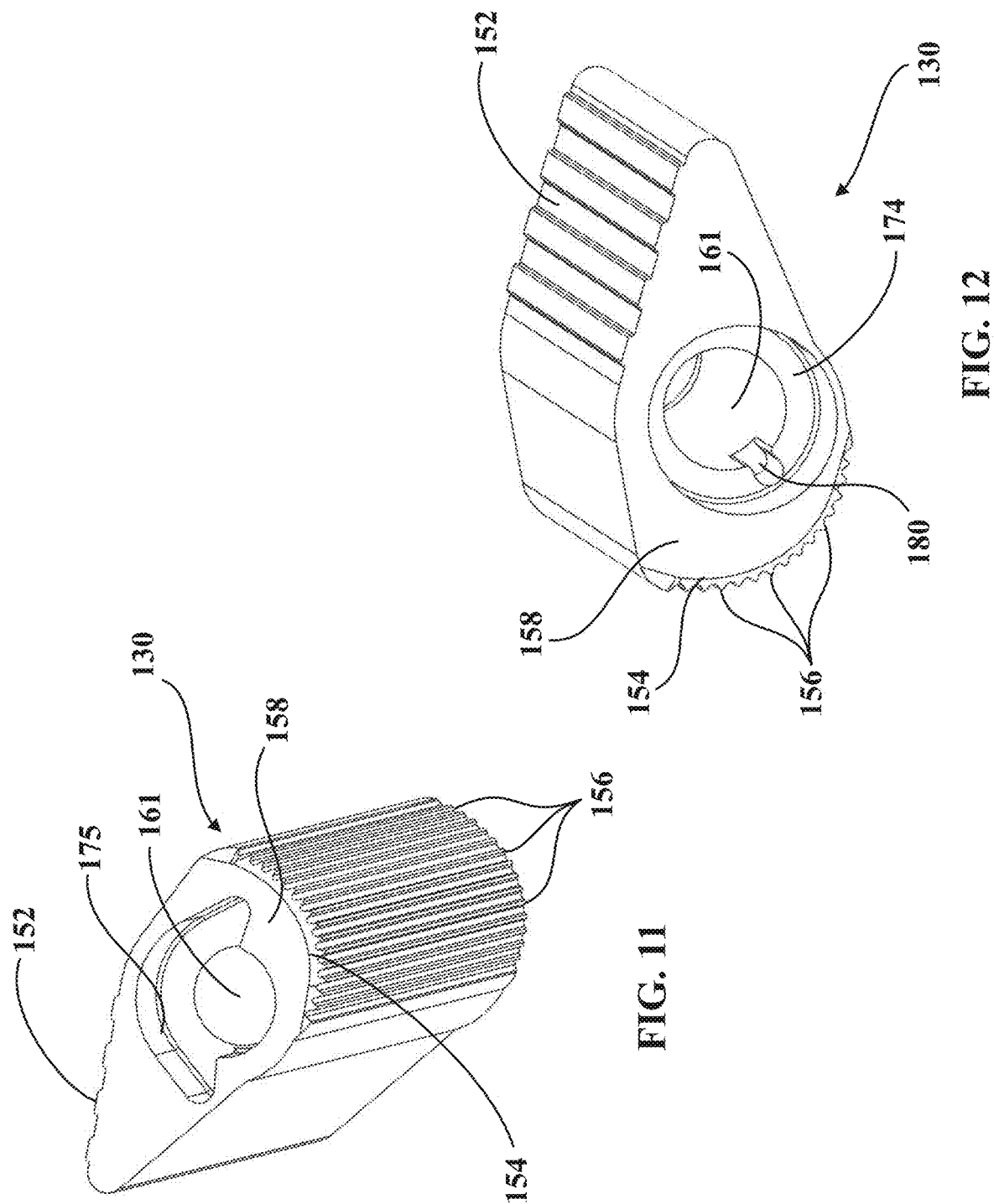

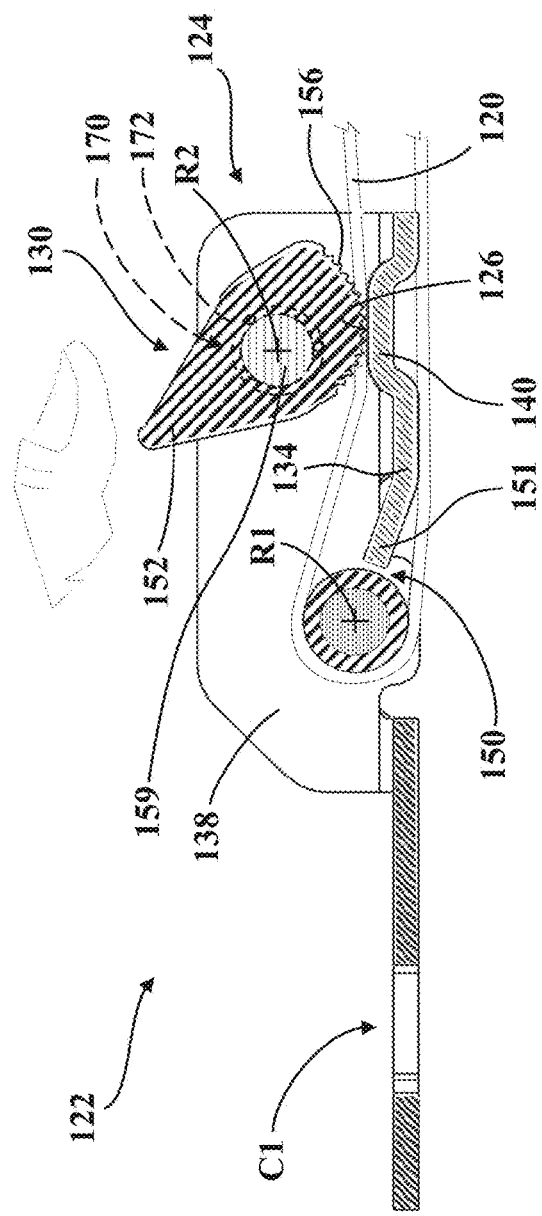
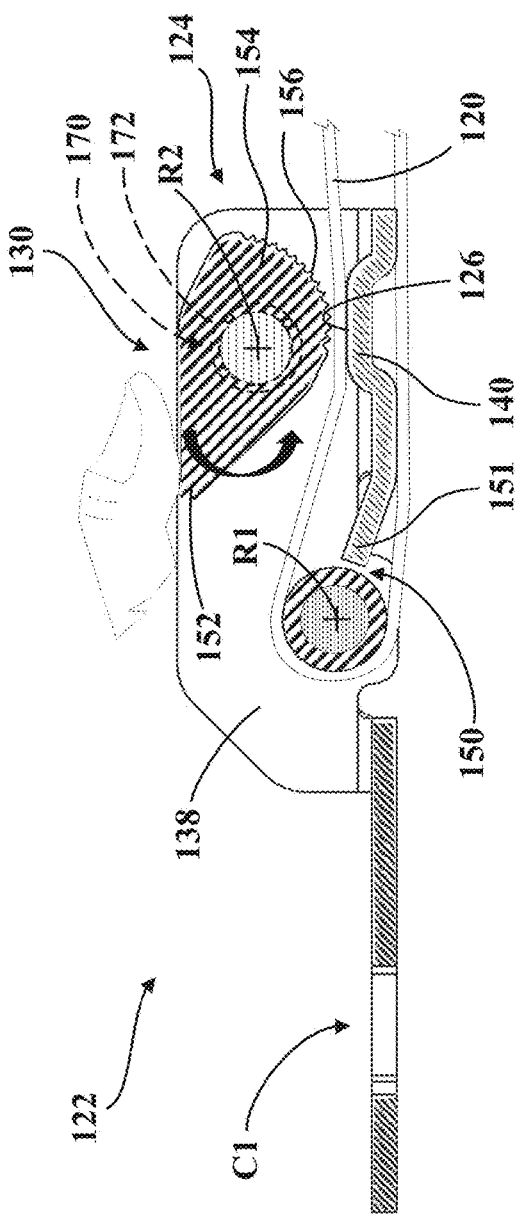
FIG. 15A
FIG. 15B

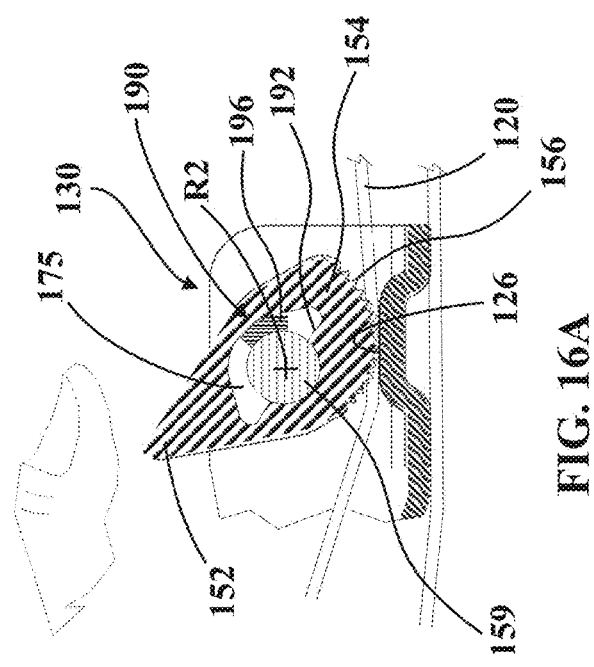 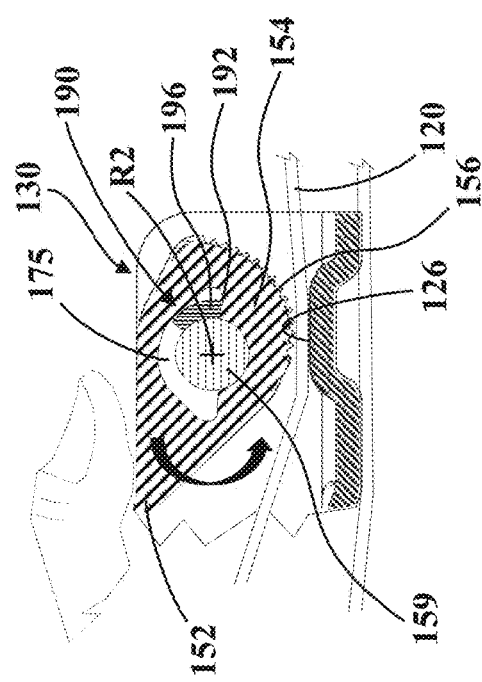

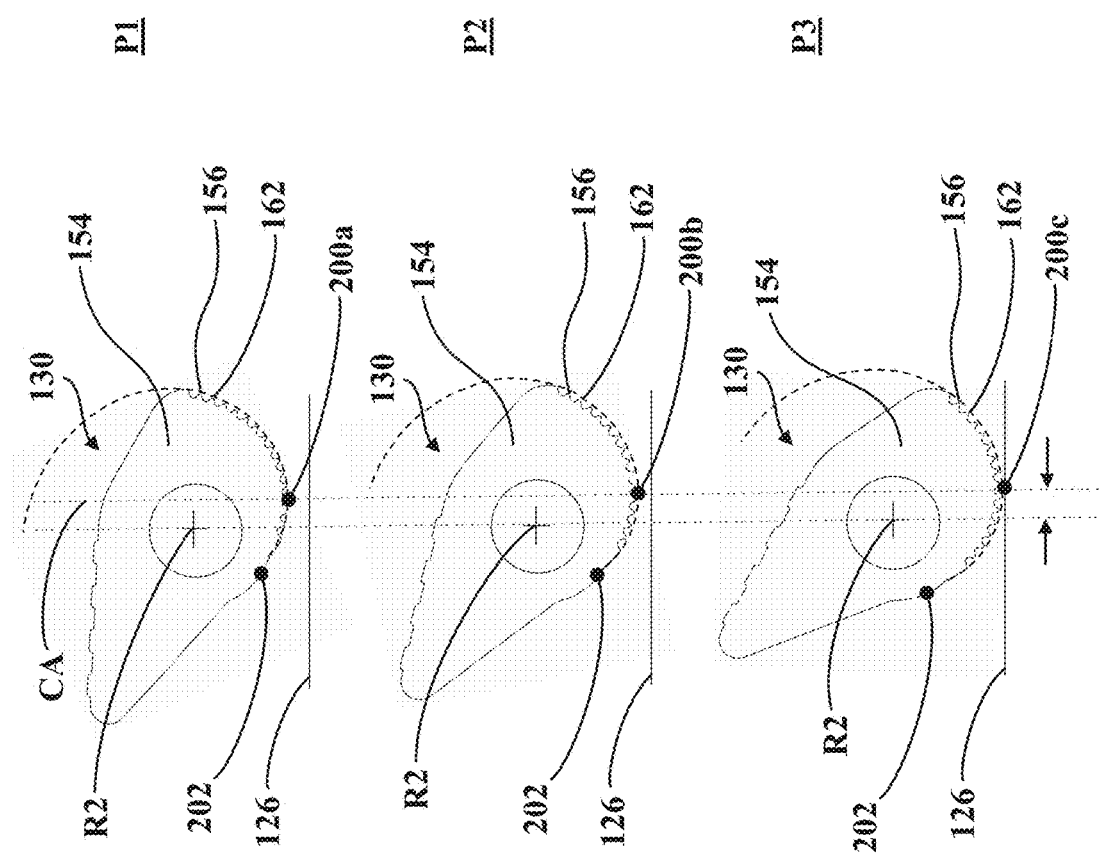

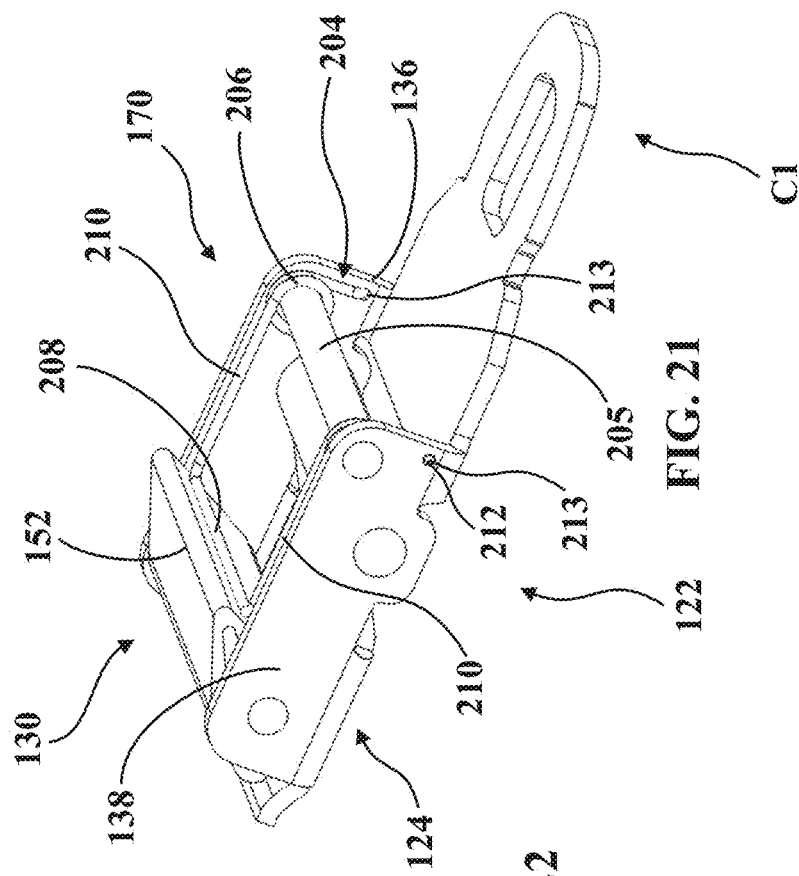
FIG. 21
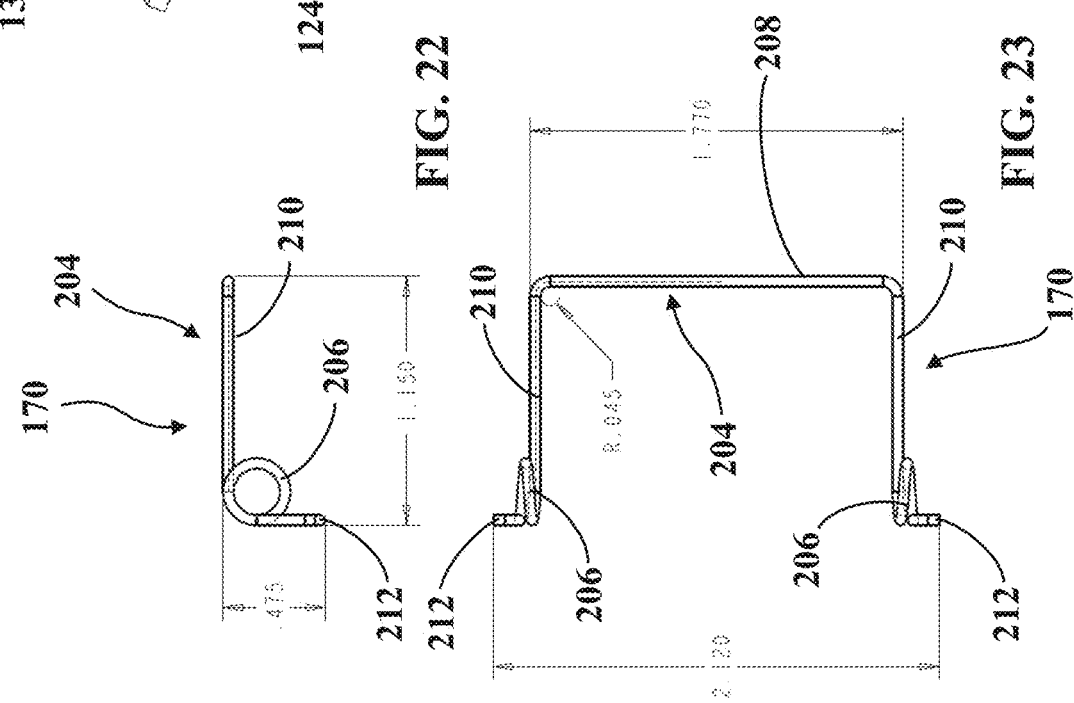
FIG. 22
FIG. 23

ADJUSTER FOR USE WITH FLEXIBLE RESTRAINTS

CROSS-REFERENCE TO RELATED APPLICATION

The subject patent application is a Continuation of U.S. patent application Ser. No. 16/281,729, filed on Feb. 21, 2019, the disclosure of which is hereby incorporated by reference in its entirety.

BACKGROUND

Patient transport apparatuses comprise, for example, hospital beds, stretchers, cots, wheelchairs, and chairs. A conventional patient transport apparatus comprises a support structure having a base, a support frame, and a patient support surface upon which the patient is supported.

In some cases, a patient transport apparatus is needed to transport a patient to a hospital or other emergency medical facility in an emergency vehicle. During transport, it is desirable for the patient to be securely restrained to the patient transport apparatus. A harness system may be used to secure the patient to the patient transport apparatus. The harness system typically comprises one or more harness assemblies having flexible restraints. Adjusters are employed to adjust an effective length of the flexible restraints.

SUMMARY

The present disclosure provides an adjuster for use with a flexible restraint. The adjuster includes a frame defining an opening and having a clamping surface. A restraint guide is coupled to the frame and is positioned relative to the opening so that the flexible restraint is capable of being routed over the clamping surface, wrapped about the restraint guide, and passed through the opening. A cam is rotatably coupled to the frame about a rotational axis, has a lever portion arranged to be actuated by a user and a clamping portion arranged to clamp the flexible restraint against the clamping surface, and is rotatable to a plurality of clamping positions. The clamping portion defines a cam profile in cross-section that has a spiral shape. The cam profile has clamping points each defined as a nearest point on the cam profile to the clamping surface at each of the plurality of clamping positions. The cam defines a fixed plane passing through the rotational axis normal to the clamping surface, and defines a clamping plane parallel to the clamping surface passing through each of the clamping points. Each of the clamping points are offset from the fixed plane by a first distance and the clamping plane is offset from the rotational axis by a second distance, with a ratio of the second distance to the first distance being in a range of from 2.5 to 5.5 for each of the clamping positions.

BRIEF DESCRIPTION OF THE DRAWINGS

FIG. 5 is a bottom perspective view of the adjuster.

FIG. 6 is a bottom view of the adjuster.

FIG. 11 is a left side perspective view of the cam.

FIG. 12 is a right side perspective view of the cam.

FIGS. 15A and 15B are cross-sectional views of the adjuster taken generally along the line 15-15 in FIG. 3 and illustrating movement of the cam to clamp and release, respectively, a flexible restraint.

FIGS. 16A and 16B are cross-sectional views of the adjuster taken generally along the line 16-16 in FIG. 3 and illustrating movement of the cam relative to the stop.

FIG. 17 is an illustration of rotational positions of the cam and clamping points on the cam profile.

FIG. 21 is a top perspective view of the adjuster with another biasing device for the cam.

FIG. 22 is a left side view of the biasing device of FIG. 21.

FIG. 23 is a bottom view of the biasing device of FIG. 21.

DETAILED DESCRIPTION

Figure 1:
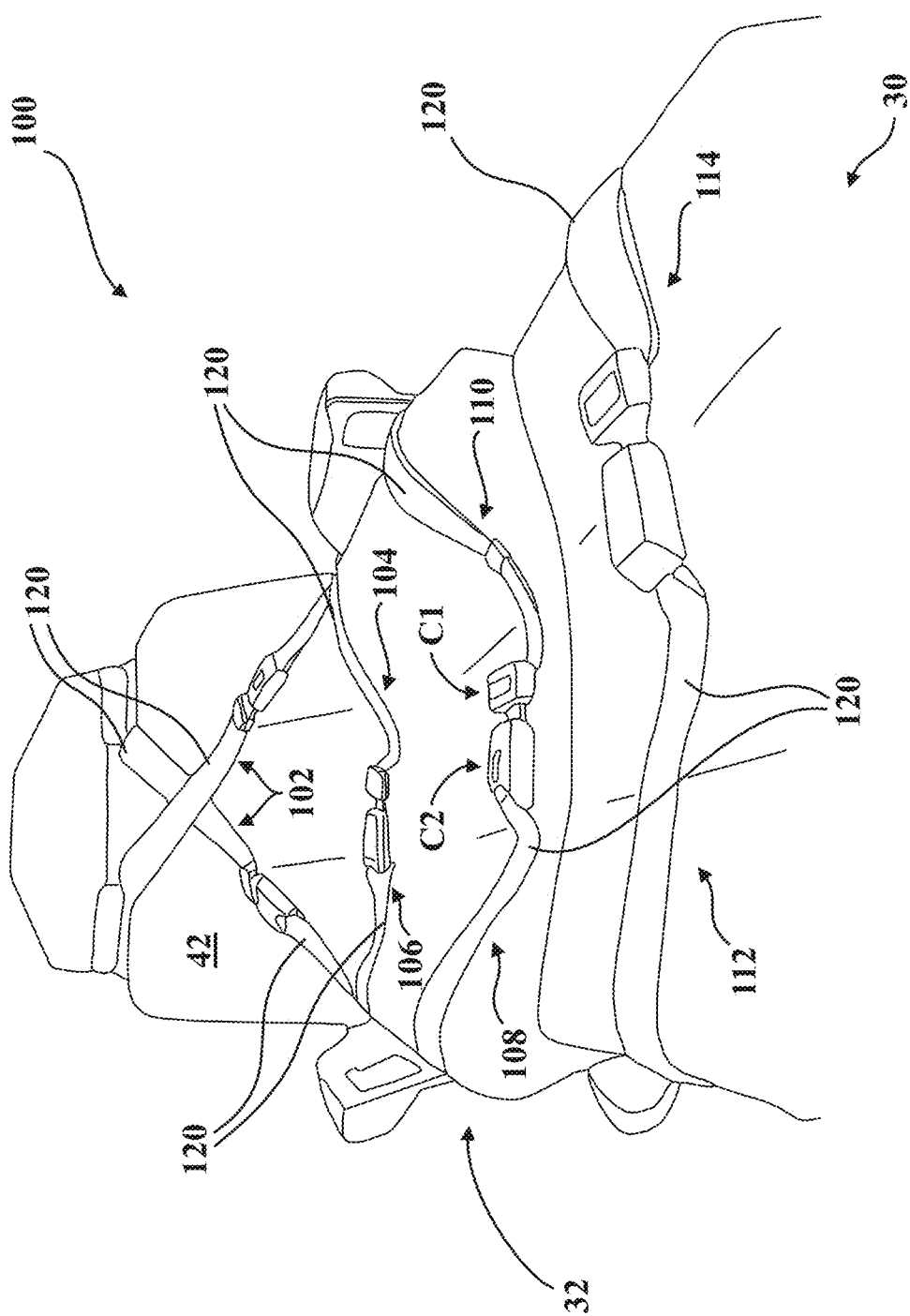
FIG. 1 is a front view of the patient transport apparatus illustrating a harness system having a plurality of harness assemblies.
Figure 2A:
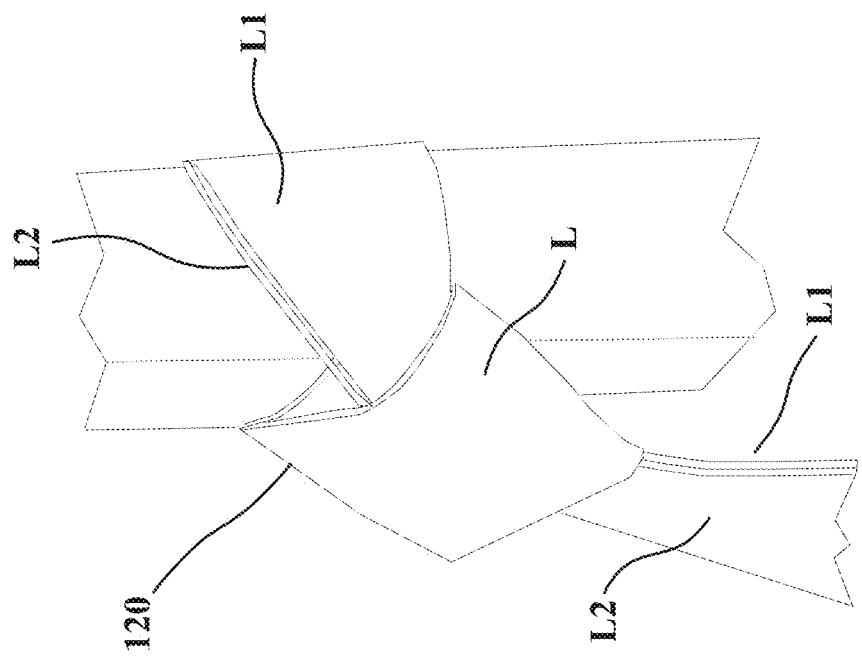
FIG. 2A is an illustration of securing a harness assembly to a support frame.

Referring to FIGS. 1 and 2A, a patient transport apparatus 30 is shown for supporting a patient. The patient transport apparatus 30 may comprise a hospital bed, stretcher, cot, wheelchair, chair, or similar apparatus utilized in the care of a patient. In the embodiment shown, the patient transport apparatus 30 comprises a cot that is utilized to transport patients in an emergency vehicle (e.g., an ambulance), such as from an emergency site to a hospital or other emergency medical facility. The patient transport apparatus 30 comprises a support structure 32 that provides support for the patient. The support structure 32 comprises a support frame 36. The construction of the support structure 32 may take on any known or conventional design.

A harness system 100 is employed on the patient transport apparatus 30 to secure the patient. The harness system 100 comprises one or more harness assemblies 102-114 that cooperate to secure the patient to the patient transport apparatus 30. For instance, in the embodiment shown in FIG. 1, the harness system 100 comprises shoulder harness assemblies 102, connecting harness assemblies 104, 106 that connect to the shoulder harness assemblies 102 and to each other, thigh harness assemblies 108, 110, and ankle harness assemblies 112, 114.

The harness assemblies 102-114 comprise elongate, flexible restraints 120. In some versions, the flexible restraints 120 comprise coated fabric. The fabric may comprise webbing, such as that formed by woven fabric. The webbing may comprise polyester webbing or other suitable materials. It is also contemplated that the fabric may be formed of nylon webbing, polypropylene webbing, cotton webbing, elastic webbing, and the like. The coated fabric may be like that described in U.S. Pat. No. 10,080,693, entitled, "Harness System for Patient Transport Apparatus," hereby incorporated herein by reference.

Referring to FIG. 2A, each of the harness assemblies 102-114 is configured to be attached to the support structure 32, but could be attached at any suitable location on the patient transport apparatus 30. In the embodiment shown, each of the harness assemblies 102-114 comprises a connecting loop L that can be utilized to attach the harness assemblies 102-114 to the support structure 32 (only one the harness assemblies 110 is shown in FIG. 2A). For instance, the connecting loop L may be passed through an opening at an anchor location A on the support structure 32 and a remainder of the harness assembly 102-114 can be passed through the connecting loop L to form a secure connection to the patient transport apparatus 30 at the anchor location A.

Figure 2B:
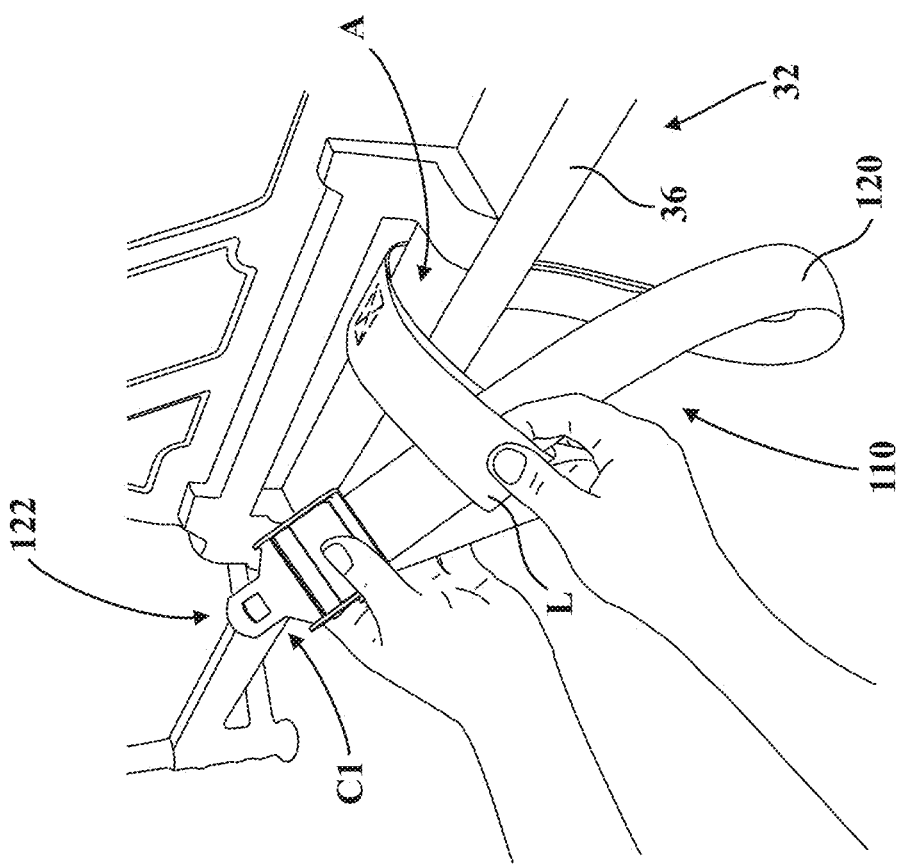
FIG. 2B is an illustration of the harness assembly secured to the support frame.

Referring to FIG. 2B, in some cases, the flexible restraint 120 may comprise two or more layers L1, L2 of fabric attached together to pass through the connecting loop L. The connecting loop L can be a source of a stress riser in the harness assembly 102-114, such as during a crash event, so the additional layer(s) of fabric act to strengthen the flexible restraint 120 at that location. In one version, two layers L1, L2 of coated fabric are adhered together (e.g., via adhesive, heat/RF welding, or ultrasonic welding) to form the connecting loop L. The two layers L1, L2 are connected together along a length of the harness assembly 102-114 so that, when the remainder of the harness assembly 102-114 passes through the connecting loop L, the portion of the harness assembly 102-114 present in the connecting loop L has the at least two layers L1, L2 of coated fabric to distribute loads. In other words, in the version shown, the layers of coated fabric that form the connecting loop L also pass through the connecting loop L when securing the harness assembly 102-114 to the support structure 32.

Adjusters 122 are used to control an effective length of the harness assemblies 102-114. More specifically, each adjuster 122 is arranged to engage the flexible restraint 120 of the harness assemblies 102-114 to adjust an effective length of the flexible restraint 120. The adjuster 122 is configured to control the effective length by being moved by a user relative to the flexible restraint 120 to vary a length of the flexible restraint 120 between the adjuster 122 and an end of the flexible restraint 120 (e.g., by sliding the adjuster 122 along the flexible restraint 120 or by pulling the flexible restraint 120 through the adjuster 122). It should be appreciated that while the harness assemblies 102-114 and adjusters 122 are described herein for use on the patient transport apparatus 30, such harness assemblies 102-114 and adjusters 122 can be used for any other suitable purpose in which a harness assembly and/or adjuster is employed (e.g., backpack harnesses, climbing harnesses, vehicle harnesses, child car seat harnesses, lifting harnesses, load-restraining harnesses, and the like).

In some versions, the adjusters 122 have integrated connectors C1 that comprise male insertion latches (e.g., tongues) configured to be received in connectors C2, such as buckles, for releasably locking to the buckles (similar to seatbelt buckles on vehicles). The connectors C1, C2 may be latches, buckles, catches, carabiners, or other suitable connectors for connecting any two of the harness assemblies 102-114 together. Such connectors are described, for example, in U.S. Pat. No. 10,080,693, entitled, "Harness System for Patient Transport Apparatus," hereby incorporated herein by reference.

Referring to FIGS. 3-10, each adjuster 122 comprises a frame 124 having a clamping surface 126 and a restraint opening 128 for routing the flexible restraint 120. A cam 130 is spring-biased to rotate relative to the frame 124 to clamp the flexible restraint 120 against the clamping surface 126 when the user has finished adjusting a location of the adjuster 122 relative to the flexible restraint 120. A restraint guide 132 guides the flexible restraint 120 during adjustment.

The frame 124 comprises a bottom wall 134 and a pair of side walls 136, 138 extending perpendicularly from the bottom wall 134 to form a U-shape. The frame 124 may comprise a single piece of material formed into a desired shape, may comprise two or more pieces connected together, or the like. The frame 124 may be formed of metal, composite materials, and/or plastic, combinations thereof, and/or any other suitable materials.

The frame 124 comprises an embossment 140 that extends between the side walls 136, 138. The embossment 140 rises above the bottom wall 134 and provides a flat surface that acts as the clamping surface 126. Owing to its flat configuration, the clamping surface 126 allows for tolerances in the adjuster 122, such as manufacturing variations in the geometry of the cam 130.

The embossment 140 also adds strength to the frame 124. The fabric forming the flexible restraint 120 may be subjected to increased tension loads during a crash event. As the tension loads increase (see arrows in FIG. 4), additional pull on the flexible restraint 120 causes the cam 130 to rotate further (e.g., clockwise in FIG. 4), which further compresses the flexible restraint 120 against the clamping surface 126. The added strength of the embossment 140 reduces deformation of the clamping surface 126 otherwise caused by such clamping forces, thereby helping to avoid uneven loads across the flexible restraint 120, which could result in side tears in the flexible restraint 120.

The restraint guide 132 is provided to guide the flexible restraint 120 relative to the adjuster 122 when adjusting a position of the adjuster 122 relative to the flexible restraint 120. The restraint guide 132 is coupled to the frame 124 and positioned relative to the restraint opening 128 so that the flexible restraint 120 is capable of being routed over the clamping surface 126, wrapped about the restraint guide 132, and passed through the restraint opening 128 (see FIG. 4).

Figure 4:
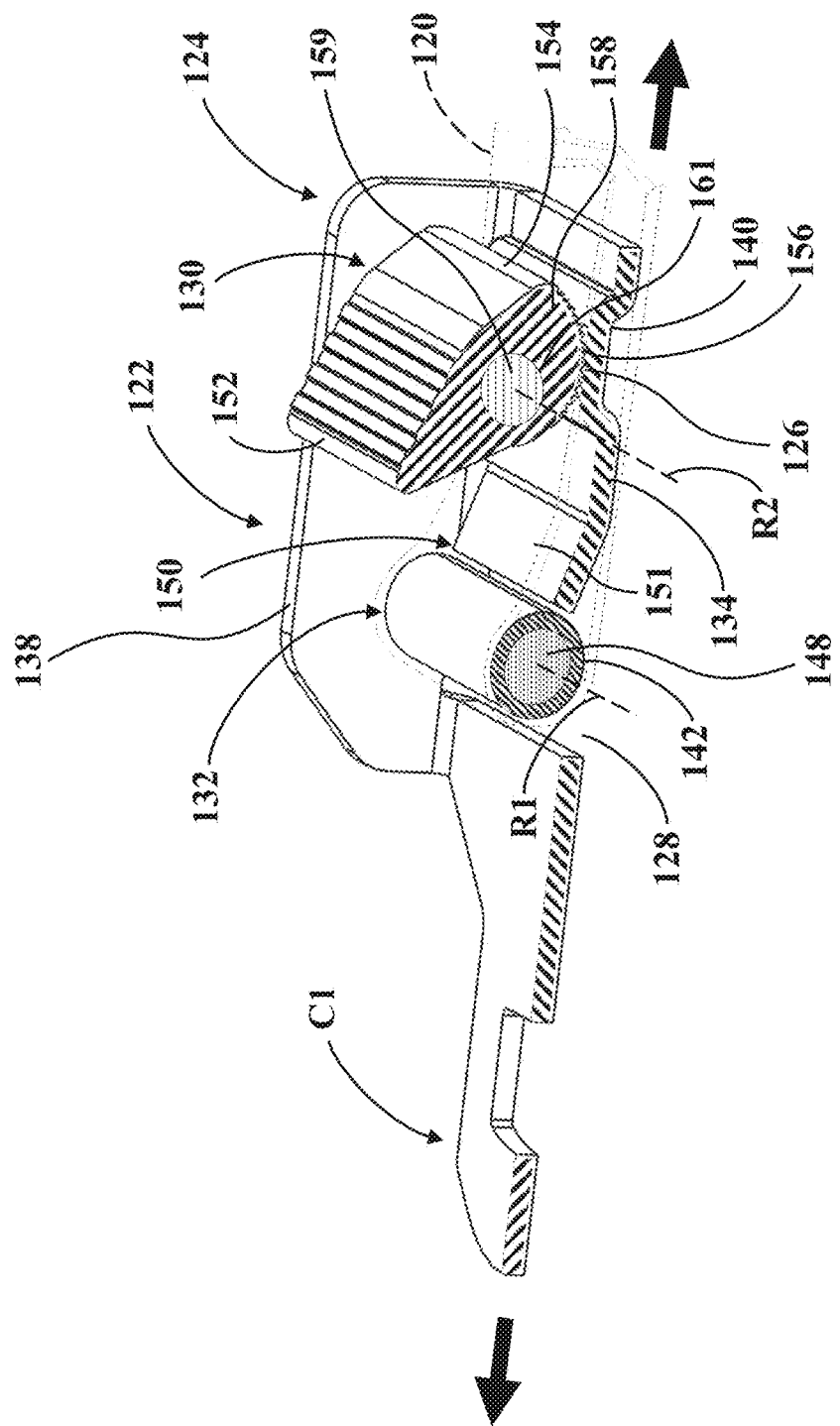
FIG. 4 is a cross-sectional view of the adjuster taken generally along the line 4-4 in FIG. 3.

In the version shown, the restraint guide 132 comprises a roller 142 rotatably coupled to the frame 124. The flexible restraint 120 wraps partially around the roller 142 during use, as shown in FIG. 4. Owing to this arrangement, the flexible restraint 120 is capable of transitioning (in direction) at least 180 degrees via the roller 142. The roller 142 rotates about a rotational axis R1 when the user releases the cam 130 from clamping the flexible restraint 120 (see, e.g., FIG.

15B) and moves the adjuster 122/flexible restraint 120 relative to each other during adjustment. In the version shown, the roller 142 is positioned so that a bottom of the roller 142 is at a slightly higher elevation than a bottom surface of the bottom wall 134 such that, under suitable tension, the flexible restraint 120 contacts the bottom surface of the bottom wall 134. Other configurations are also possible.

A pin 144 rotatably couples the roller 142 to the frame 124. The pin 144 comprises a head 146 (see FIG. 3). A shaft 148 extends from the head 146 to support the roller 142. The shaft 148 passes through openings in the side walls 136, 138 (see FIG. 7) and is secured to the frame 124 via a rivet, nut, welding, and/or any other suitable fastener. The pin 144 may be fixed to the frame 124 or may be rotatable relative to the frame 124. In the version shown, the pin 144 acts as an axle about which the roller 142 rotates relative to the frame 124.

Figure 3:
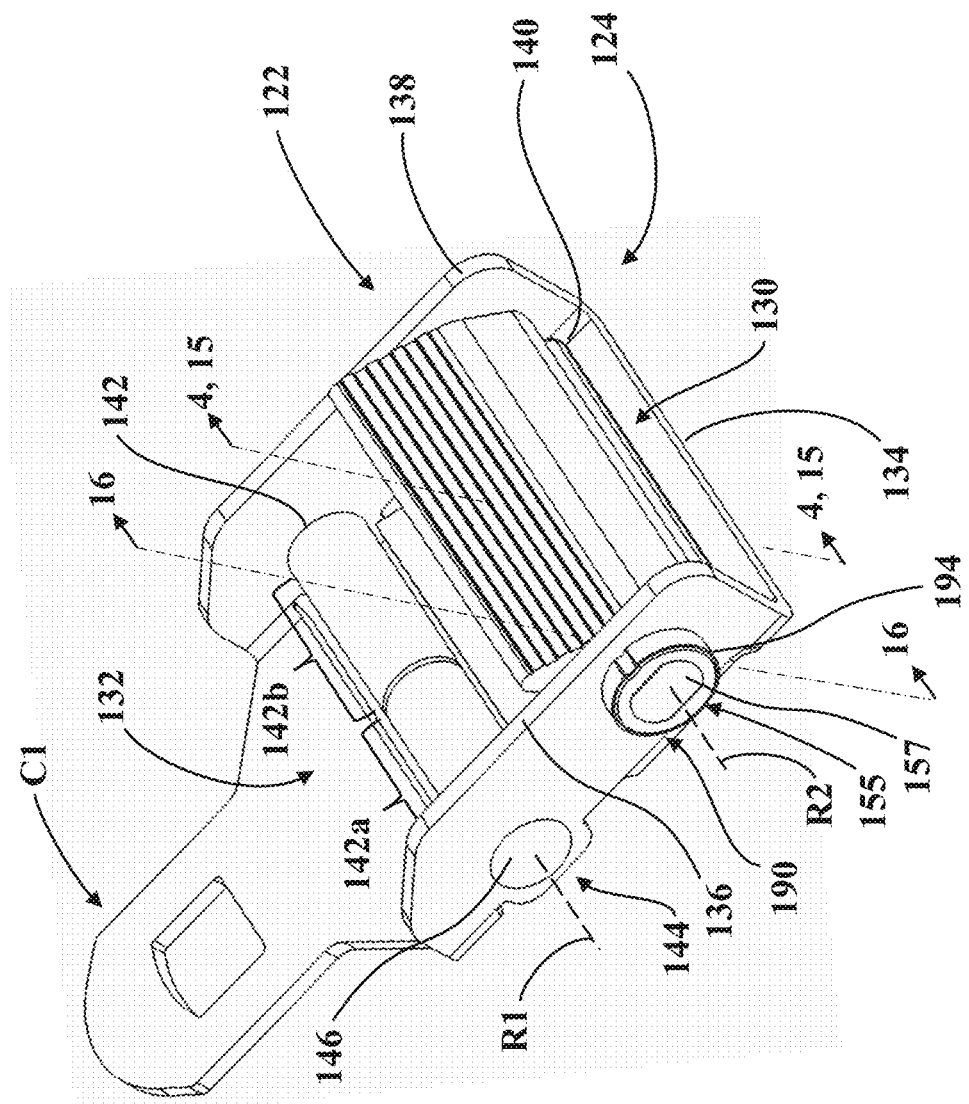
FIG. 3 is a top perspective view of an adjuster of the harness assembly.

The roller 142 may comprise one or more rolling segments 142a, 142b (see FIG. 3). In some cases, the rolling segments 142a, 142b may be capable of rotating relative to each other. The roller 142 and the pin 144 may be formed of metal, composite materials, and/or plastic, combinations thereof, and/or any other suitable materials. In some embodiments, the restraint guide 132 may additionally, or alternatively, comprise a fixed surface, fixed bar, knurled bar, and/or any other suitable guide for guiding the flexible restraint 120 during adjustment.

Figure 4A:
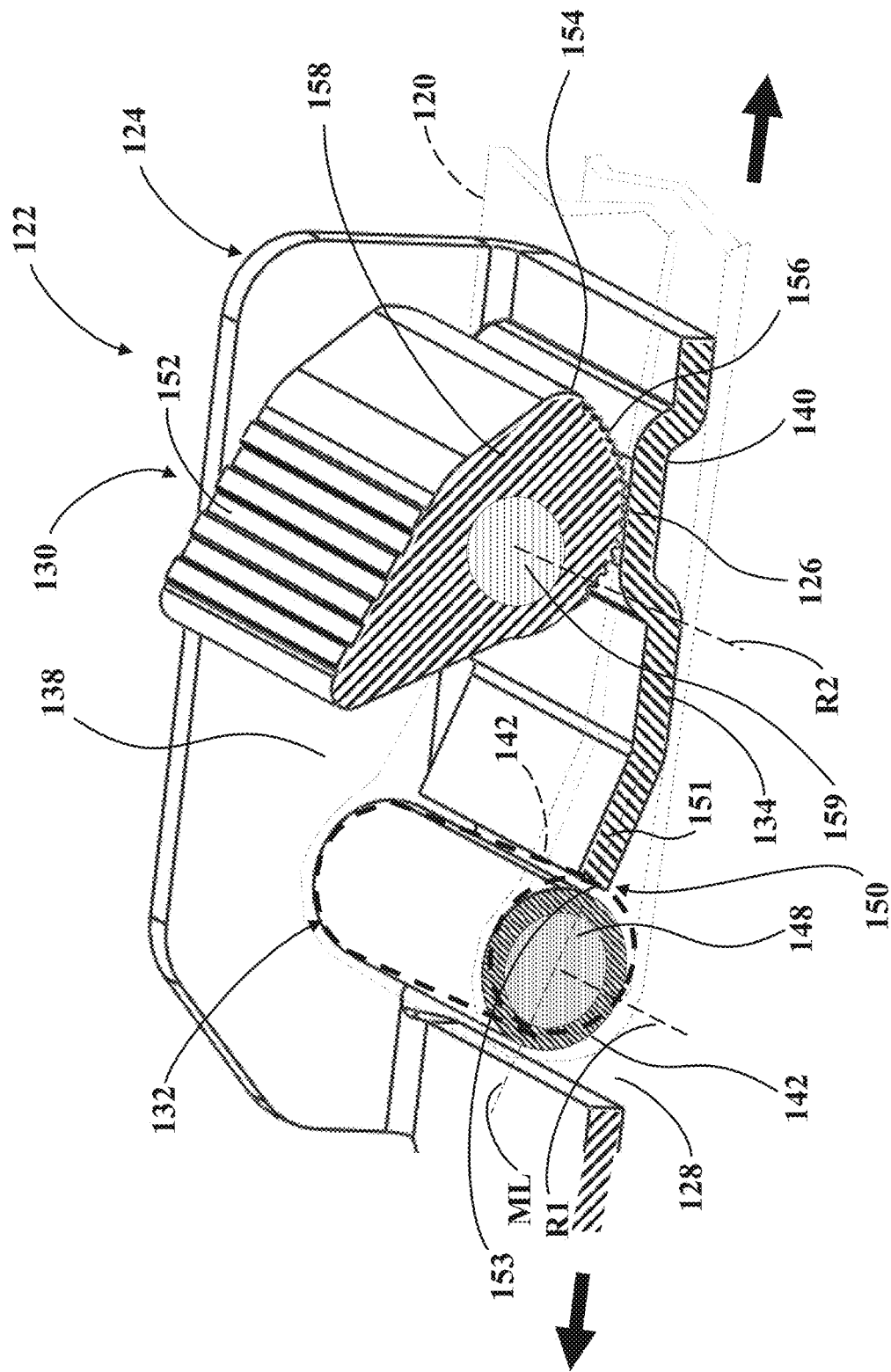
FIG. 4A is an illustration of bending of a restraint guide of the adjuster.
Figure 7:
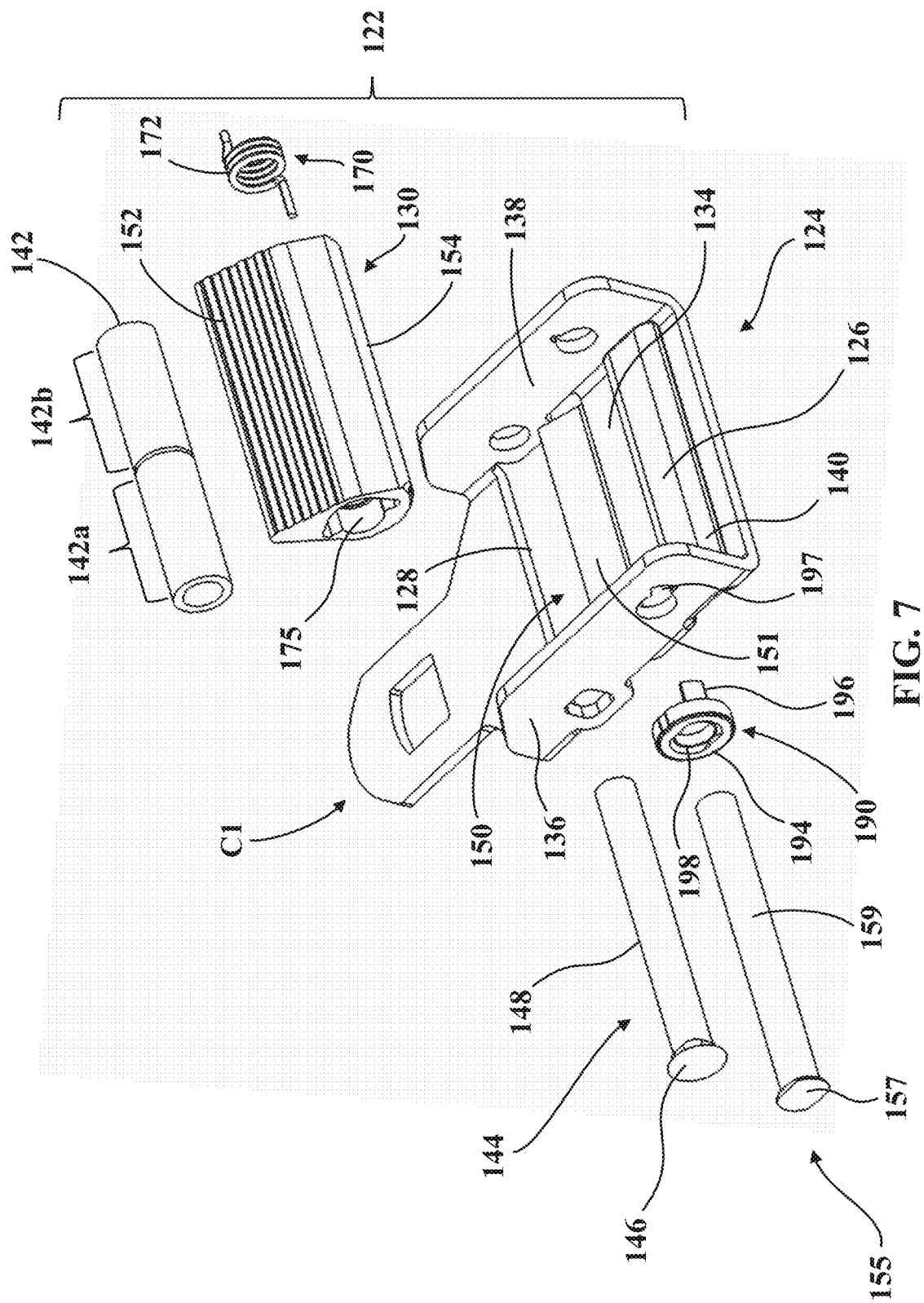
FIG. 7 is an exploded perspective view of the adjuster.

Referring to FIG. 4A, in addition to the cam 130, a brake 150 may be employed to help arrest movement of the flexible restraint 120 relative to the adjuster 122 during high tension loads (see arrows), such as during a crash event. The brake 150 acts against the roller 142 during such events to prevent rotation of the roller 142 relative to the frame 124, and thus to provide additional friction via sliding of the flexible restraint 120 on the roller 142. In the version shown, the brake 150 forms part of the frame 124, and is defined by a flanged portion 151 of the bottom wall 134. In the version shown, the flanged portion 151 forms an obtuse angle with a main portion of the bottom wall 134. The obtuse angle may be greater than 90 degrees and less than 180 degrees, from 135 degrees to 175 degrees, from 150 degrees to 170 degrees, or any suitable angle.

The brake 150 is spaced from the roller 142 in normal operation, and contacts the roller 142 upon bending of the restraint guide 132 (e.g., bending of the pin 144 and/or rolling segments 142a, 142b) during high tension loads, to brake rotation of the roller 142 (see hidden lines illustrating such bending and showing contact with the roller 142). Thus, the cam 130 of the adjuster 122 acts as a primary locking mechanism that restricts motion of the flexible restraint 120 and absorbs energy and the brake 150 acts as a secondary locking mechanism. The brake 150 further provides additional structure to prevent the pin 144 and/or roller 142 from bending beyond failure in certain situations. For instance, the pin 144 and/or roller 142 are only able to bend slightly before engaging the flanged portion 151 owing to a small gap between an outer surface of the roller 142 and the flanged portion 151. The gap may have a distance (shortest distance from roller 142 to flanged portion 151) of from 0.01 to 0.2 inches, from 0.05 to 0.2 inches, from 0.05 to 0.1 inches, or the like. The flanged portion 151 may have a flat end surface 153 arranged to engage the roller 142 normal to the roller 142. In some cases, a midline axis ML of the flanged portion 151 (see FIG. 4A) passes through the rotational axis R1.

Referring specifically to FIGS. 4 and 11-16B, the cam 130 is rotatably coupled to the frame 124 about a rotational axis R2, which is parallel to rotational axis R1 in some versions. The cam 130 comprises a lever portion 152 arranged to be actuated by the user and a clamping portion 154 opposite the lever portion 152. The lever portion 152 comprises a textured surface for being engaged by a finger of the user to rotate the cam 130 to a releasing position thereby releasing the cam 130 from the flexible restraint 120 for purposes of adjustment (see, e.g., FIG. 15B). The clamping portion 154 is arranged to clamp the flexible restraint 120 against the clamping surface 126 during normal operation (see FIG. 15A). The cam 130 is rotatable from the releasing position to a plurality of clamping positions (see, e.g., FIGS. 4 and 15A). There are various clamping positions owing to the variation in thickness of the flexible restraints 120 that may be used with the adjuster 122 and owing to the amount of tension placed on the harness assembly 102-114, which can increase the clamping force of the cam 130, and thus its rotational position relative to the frame 124.

A pin 155 rotatably couples the cam 130 to the frame 124. The pin 155 comprises a head 157 (see FIG. 3). A shaft 159 extends from the head 157 to support the cam 130 via a through hole 161 in the cam 130. The shaft 159 passes through openings in the side walls 136, 138 (see FIG. 7) and is secured to the frame 124 via a rivet, nut, welding, and/or any other suitable fastener. The pin 155 may be fixed to the frame 124 or may be rotatable relative to the frame 124. In the version shown, the pin 155 acts as an axle about which the cam 130 rotates relative to the frame 124. The cam 130 and the pin 155 may be formed of metal, composite materials, and/or plastic, combinations thereof, and/or any other suitable materials. In some versions, the cam 130 is formed of plastic, such as nylon (e.g., nylon 6, nylon 66), acrylonitrile butadiene styrene (ABS), polycarbonate, polyphenylsulfone (PPSU), ultra high molecular weight (UHMW) polyethylene, or the like.

Figure 14:
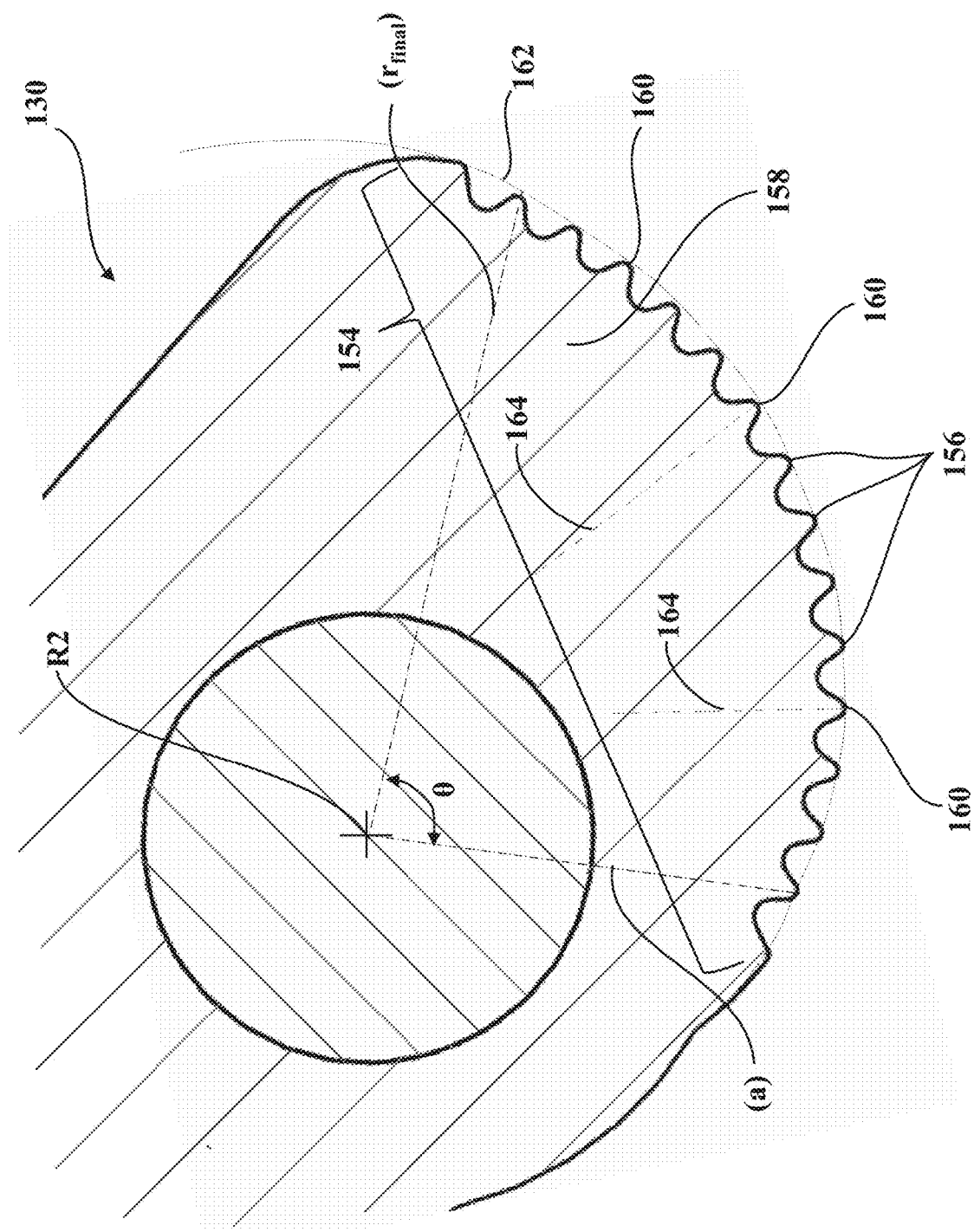
FIG. 14 is a close-up view of teeth of the cam and a spiral-shaped cam profile.

The clamping portion 154 of the cam 130 comprises teeth 156 shaped to engage and grip the flexible restraint 120 during use to limit slipping of the flexible restraint 120 relative to the adjuster 122. The teeth 156 extend from a body 158 of the cam 130 to tips 160 (see FIG. 14). As will described in greater detail below, the tips 160 of the teeth 156, when viewed in cross-section perpendicular to the rotational axis R2, define a cam profile 162 having a spiral shape (see, e.g., FIG. 14). More specifically, the tips 160 lie along a spiral defined about the rotational axis R2, as shown in FIG. 14. In the version shown, the spiral is an Archimedean spiral or arithmetic spiral defined by the equation ($r=a+b*\theta$), where ($r$) and ($\theta$) are the polar coordinates of the spiral and parameters (a), (b) define an initial radius of the spiral and the distance between successive turns (if they were present), respectively. In the version shown in FIG. 14, the initial radius (a), which is defined from the rotational axis R2 to the tip 160 of the closest tooth, is about 0.24 inches, and the parameter (b) is about 0.0015. In this version, a final radius ($r_{final}$) from the rotational axis R2 to the tip 160 of the farthest tooth is about 0.37 inches and the angle ($\theta$) between the radiuses (a), ($r_{final}$) is about 84 degrees. So, for example, the equation is satisfied as follows: $r_{final}$=0.37=0.24+(0.0015)*(84). Other versions with different parameters defining the spiral are also contemplated. Each of the teeth 156 has a generally triangular shape in the cross-section and is symmetrical about a midline 164 disposed normal to the cam profile 162.

Figure 13:
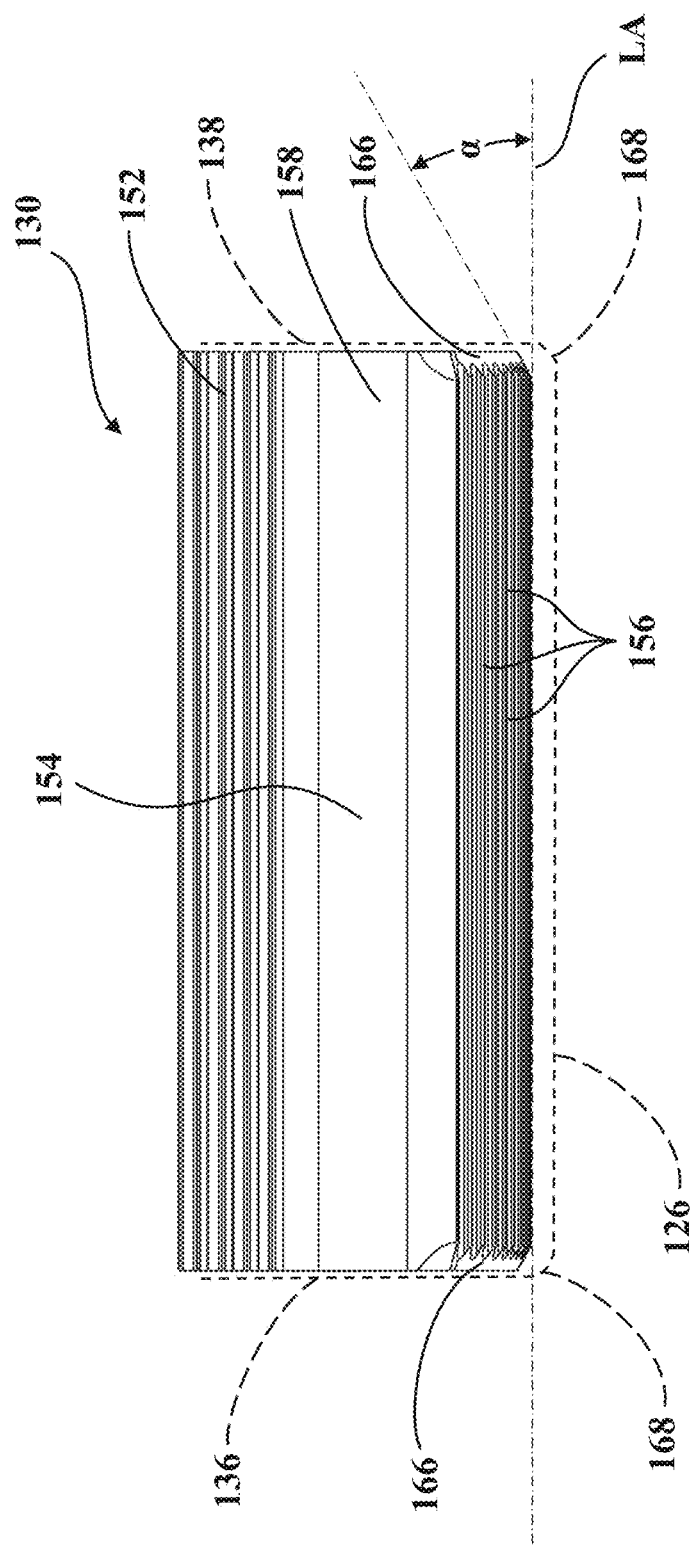
FIG. 13 is a rear view of the cam.

In the version shown, referring to FIG. 13, chamfers 166 are formed in the clamping portion 154 so that the teeth 156 terminate short of the sides of the cam 130. The chamfers 166 help to prevent the clamping portion 154 of the cam 130 from catching the flexible restraint 120 at radii 168 between the clamping surface 126 of the embossment 140 and inner surfaces of the side walls 136, 138, which could otherwise reduce the clamping force on the flexible restraint 120 allowing the flexible restraint 120 to slip relative to the adjuster 122. In other words, if the cam 130 was otherwise constrained from reaching the clamping surface 126 by virtue of engaging a point along the radii instead, then the cam 130 may not effectively clamp the flexible restraint 120 against the clamping surface 126. The chamfers 166 may be formed at any suitable angle α to provide clearance with the radii 168, such as less than 45 degrees relative to a longitudinal axis LA of the cam 130. The radii 168 may be minimized or reduced to increase contact area with the flexible restraint 120 and mitigate or eliminate edge contact between the teeth 156 of the cam 130 and radii 168. More specifically, by minimizing or reducing the radii 168, the flat area of the clamping surface 126 is increased, thereby providing increased area for clamping.

Referring to FIGS. 8-10, 15A, and 15B, a biasing device 170 acts between the frame 124 and the cam 130 to bias the cam 130 toward the plurality of clamping positions. Thus, the cam 130 is normally biased into a clamping position, as shown in FIG. 15A. The spring-biased nature of the cam 130 allows the flexible restraint 120 to move freely in one direction (e.g., to the right in FIG. 15A when shortening the effective length of the flexible restraint 120), while locking in the other direction (e.g., to the left in FIG. 15A), unless manually released by the user, as shown in FIG. 15B.

Figure 8:
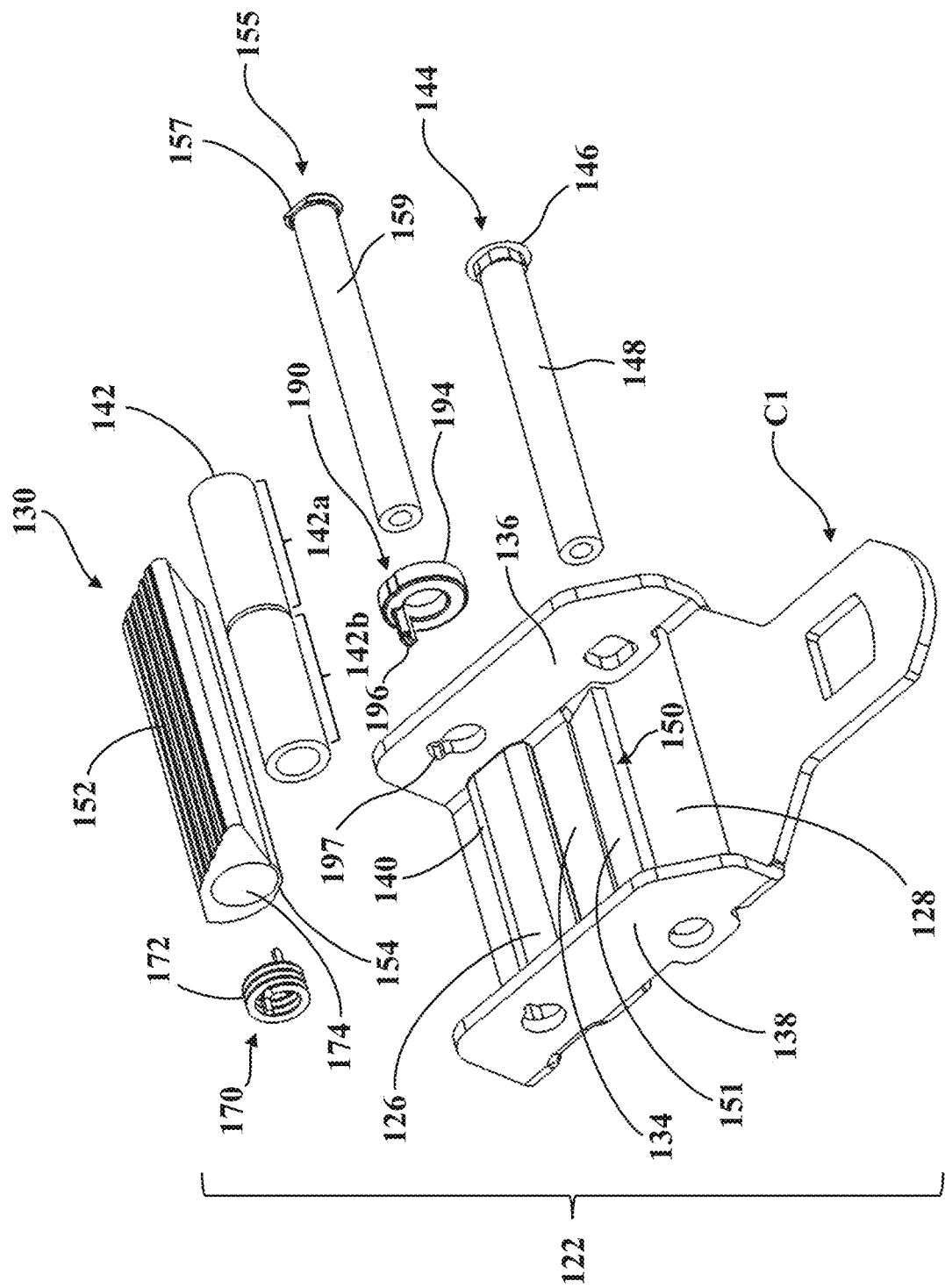
FIG. 8 is another exploded perspective view of the adjuster.
Figure 9:
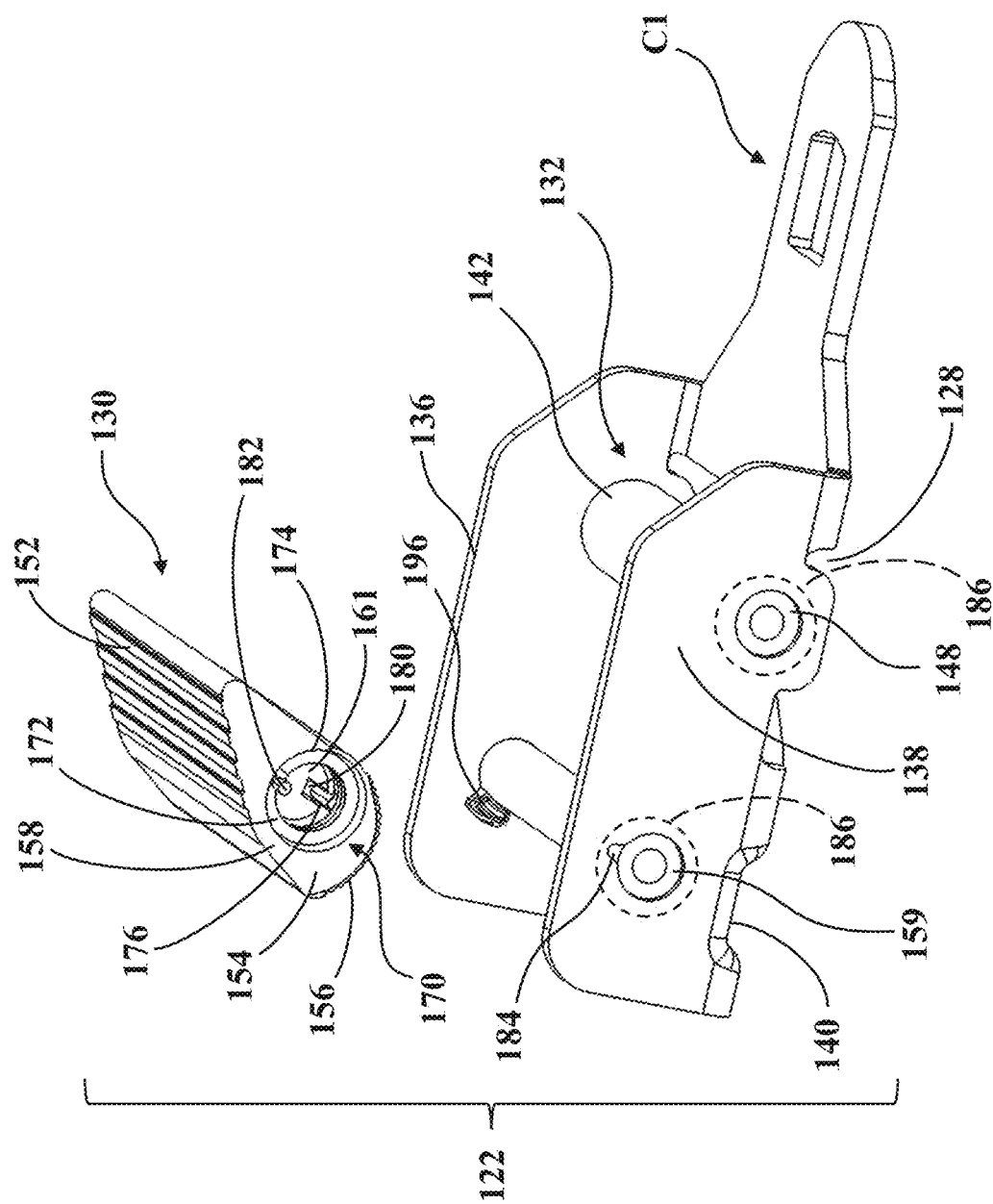
FIG. 9 is a partial exploded perspective view of the adjuster illustrating a cam and biasing device.
Figure 10:
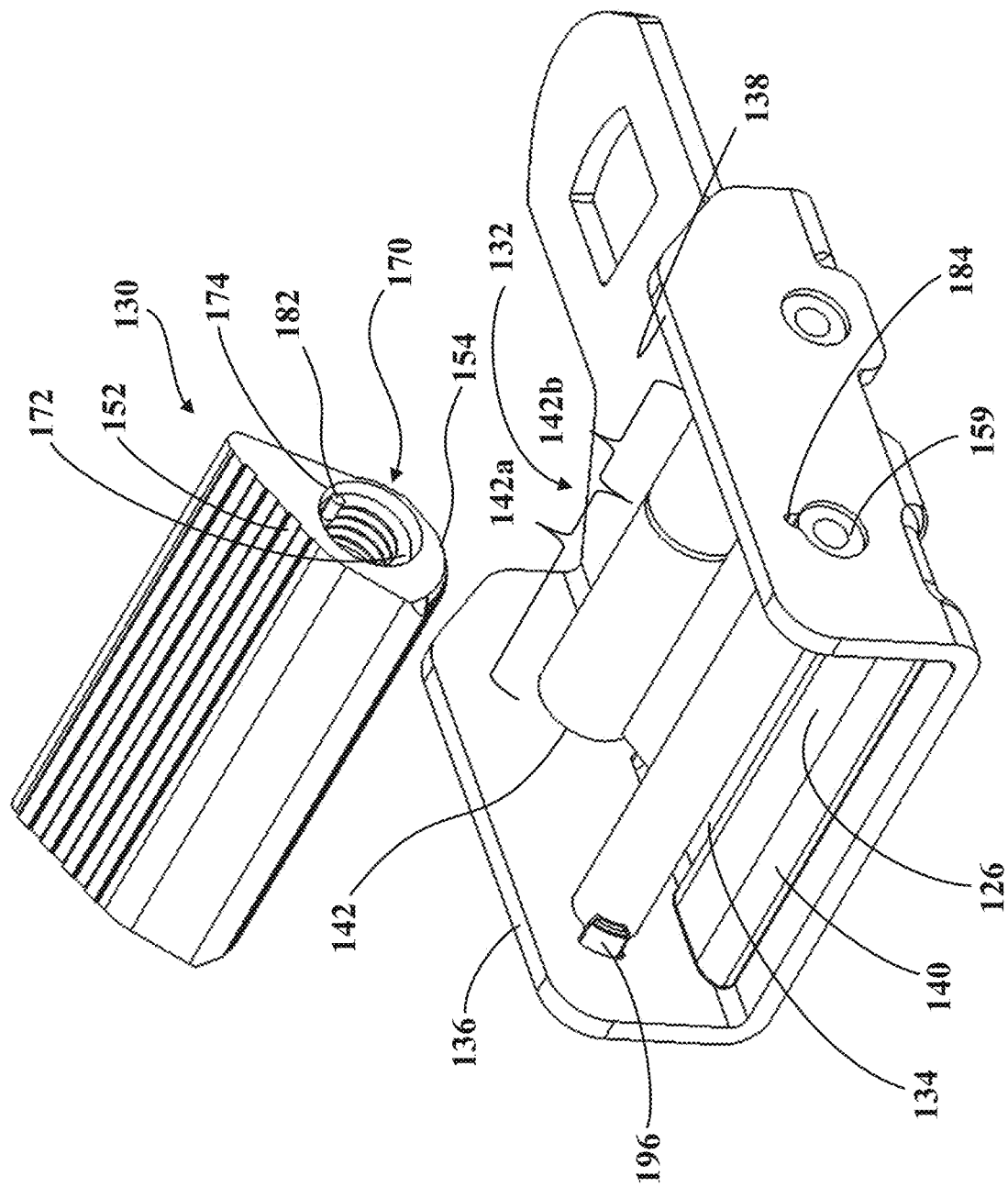
FIG. 10 is a close-up view from FIG. 9 showing a stop for the cam.

The biasing device 170 may comprise a spring 172, such as a torsion spring disposed about the shaft 159 of the pin 155 (see, e.g., FIGS. 8-10). The cam 130 may define a spring pocket 174 on one side to receive the spring 172 (see, e.g., FIGS. 8-10) so that the spring 172 is at least partially hidden from view of the user and inaccessible by the user, without disassembling the adjuster 122. In some versions, the spring 172 may be fully hidden and completely inaccessible by the user. The spring 172 may be present on only one side of the cam 130 in the spring pocket 174, yet a pocket 175 of the same depth may be formed in an opposing side of the cam 130. By employing pockets of the same depth on both sides of the cam 130, loading on the flexible restraint 120 is better balanced. In addition, the spring 172 may be a double offset spring to minimize the likelihood of bending and undesirable jamming of the spring 172. The spring 172 may have opposing tangs 176, 182. The tang 176 is inserted into a tang pocket 180 defined in the cam 130 through the spring pocket 174 (see FIG. 9). The other tang 182 is inserted into an aperture 184 defined through the side wall 138. An end 186 of a fastener (e.g., rivet, nut, etc.) used to secure the shaft 159 to the frame 124 may cover the tang 182 of the spring 172 (see hidden lines in FIG. 9).

Referring to FIGS. 7, 10, 16A and 16B, a stop 190 is coupled to the frame 124 and is arranged to engage the cam 130 upon rotation of the cam 130 by the user from one of the clamping positions to the releasing position. The pocket 175 in the cam 130 is shaped and sized to receive the stop 190. Further, the cam 130 defines an abutment 192 (also referred to as a shoulder) at one end of the pocket 175 arranged to engage the stop 190 upon rotation of the cam 130 by the user to the releasing position. The stop 190 comprises a collar 194 disposed about the pin 155 and a protrusion 196 extending from the collar 194. The protrusion 196 extends through an opening 197 in the side wall 136 (see FIG. 10) and into the pocket 175. The opening in the side wall 136 for the protrusion 196 is sized so that the protrusion 196 is able to fit therethrough, but the protrusion 196 is substantially unable to move in the opening. In other words, the protrusion 196 is effectively fixed to the frame 124.

The collar 194 defines an opening 198 sized to receive the head 157 of the pin 155 and shaped to prevent relative rotation between the pin 155 and the collar 194. In one version, the head 157 and opening 198 having mating double-D shapes to prevent relative rotation between the pin 155 and the collar 194. Other anti-rotation features are also contemplated to prevent relative rotation between the pin 155 and the collar 194.

Operation of the stop 190 is best shown in FIGS. 16A and 16B. In particular, FIG. 16A illustrates the stop 190 being located in the pocket 175 spaced from the abutment 192 when the cam 130 is in one of the clamping positions. The pocket 175 is sized to allow the stop 190 to travel in the pocket 175 as the cam 130 moves to and between the plurality of clamping positions. FIG. 16B illustrates the user releasing the cam 130 by pressing the lever portion 152 and rotating the cam 130 (e.g., counterclockwise in FIG. 16B) until the protrusion 196 of the stop 190 engages and abuts the abutment 192. At this point, the user is unable to further rotate the cam 130 by pressing the lever portion 152. Upon releasing the lever portion 152, the spring-bias applied to the cam 130 returns the cam 130 to the position shown in FIG. 16A. In some cases, the stop 190 is provided to prevent over rotation of the cam 130, which could cause plastic deformation of the spring 172.

FIG. 17 further illustrates the cam profile 162 (in cross-section) at three different clamping positions P1, P2, P3 (e.g., at three different rotational positions of the cam 130). The cam profile 162 comprises a different clamping point 200a, 200b, 200c at each of the different clamping positions P1, P2, P3. Each of the clamping points 200a, 200b, 200c is defined as a nearest point on the cam profile 162 to the clamping surface 126. In the version shown, the clamping points 200a, 200b, 200c are defined as the lowermost points on the cam profile 162, closest to the clamping surface 126. Thus, as the cam 130 rotates to further compress the flexible restraint 120, or to press against a thinner flexible restraint 120, the clamping points 200a, 200b, 200c change by moving closer to the clamping surface 126. At the same time, the clamping points 200a, 200b, 200c change by moving along the cam profile 162 further from a starting point 202 of the cam profile 162 (compare the distance of the clamping points 200a, 200b, 200c from the starting point 202 at each of the clamping positions P1, P2, P3). In the version shown, even though the clamping points 200a, 200b, 200c move further from the starting point 202, all of the clamping points 200a, 200b, 200c substantially lie on a common clamping axis CA normal to the clamping surface 126. It should be appreciated that substantially lying on the clamping axis CA includes clamping points that are slightly off the clamping axis CA, such as clamping points that are within 0.005 inches or less of the clamping axis CA, within 0.002 inches or less of the clamping axis CA, or within 0.001 inches or less of the clamping axis CA. Other configurations of the cam 130 are also contemplated, including, for example, versions in which the clamping points move to the right of the clamping axis CA as the cam 130 rotates.

Figures 18A, 18B, 19:
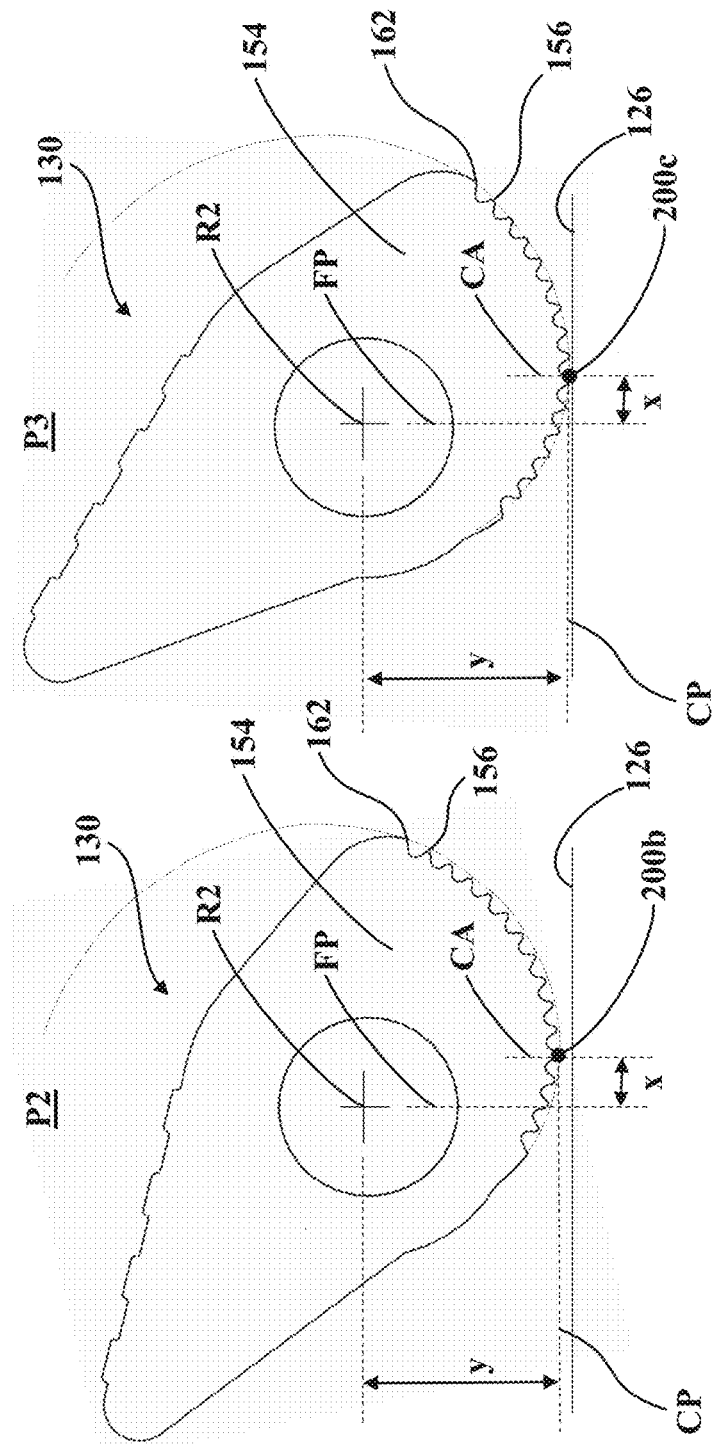
FIGS. 18A and 18B illustrate the cam at two different, rotational positions and variables used to evaluate a relationship of the clamping position to clamping force.
FIG. 19 is a table of values for distances (x) and (y) from FIGS. 18A and 18B.

Referring to FIGS. 18A and 18B, the clamping positions P2 and P3 of the cam 130 are shown along with variables that affect performance of the cam 130 in certain embodiments. Two of these variables include a first distance (x) and a second distance (y). As shown, the cam 130 defines a fixed plane FP passing through the rotational axis R2 and normal to the clamping surface 126. The cam 130 also defines a clamping plane CP parallel to the clamping surface 126 and passing through each of the clamping points 200b, 200c, which may be a tangent plane, defined tangent to the cam profile 162 at the particular clamping point. Each of the clamping points 200b, 200c (and the associated clamping axis CA) are offset from the fixed plane FP by the first distance (x) and the clamping plane CP is offset from the rotational axis R2 by the second distance (y). A ratio of the second distance (y) to the first distance (x) falls within a range of from 2.5 to 5.5, from 2.7 to 4.3, or from 3.0 to 4.0. In some versions, the first distance (x) is from 0.05 inches to 0.1 inches and the second distance (y) is from 0.15 inches to 0.4 inches. In some versions, the first distance (x) at the clamping positions P1, P2, P3 is relatively constant, such as being within a deviation of +/−0.005 inches, +/−0.002 inches, or +/−0.001 inches.

The table shown in FIG. 19 illustrates sample values for the first distance (x) and the second distance (y) at four clamping positions, including the clamping positions P1, P2, P3 (e.g., 15 degrees, 30 degrees, and 45 degrees of rotation). As shown, the first distance (x) is substantially constant between the different clamping positions, the second distance (y) increases with rotation owing to the nature of the cam profile 162 of the cam 130, and the ratio of the second distance to the first distance (y/x) falls within a range of 3.0 to 4.0. Another variable shown in the table is the change in nearest distance (Delta y) from the cam profile 162 to the clamping surface 126 starting from an initial clamping position (0 degrees). Owing to the shape of the cam profile 162, at each increment of rotation (e.g., 15 degrees), the change in distance (Delta y) increases by 0.022 inches. Accordingly, the change in nearest distance (Delta y) from the initial clamping position to: the first clamping position P1 is 0.022 inches; to the second clamping position P2 is 0.022*2 or 0.044 inches; and to the third clamping position P3 is 0.022*3 or 0.066 inches.

Figure 20:
FIG. 20 is a chart illustrating the ratio of y/x relative to delta y.

As shown in FIG. 20, a chart of the ratio (y/x) relative to the change in nearest distance (Delta y) is substantially linear and nearly constant. It has been found that the clamping force provided by the cam 130 is related to the ratio (y/x). The spiral geometry of the cam profile 162 helps to keep the ratio (y/x) consistent throughout the rotation of the cam 130 and prevent large variations in the clamping force, even with variations in manufacturing tolerance. In some versions, the first distance (x) and the second distance (y) can be measured relative to the tip 160 of the active tooth 156 (e.g., the lowermost tooth that engages the flexible restraint 120) at each of the plurality of clamping positions P1, P2, P3.

FIGS. 21-23 illustrate another example of the biasing device 170 that could be employed to bias the cam 130 toward the plurality of clamping positions. In this example, the biasing device 170 comprises a dual torsion spring 204 having coils 206 disposed about a spring-supporting pin 205. The spring-supporting pin 205 is coupled to the frame 124. The spring-supporting pin 205 may be fixed to the frame 124, such as by rivets, nuts, welding, or the like. When rivets are employed on the spring-supporting pin 205, or any of the other pins described herein, the shaft of the pin may comprise blind holes in both ends that are pop-riveted into place. The rivets thereby provide a cover to both ends of the shaft and provide adequate strength, even with a relatively small diameter. An example of such blind holes are shown in FIGS. 9 and 10 in which the shafts 148, 159 are shown without their associated rivets that would attach to the shafts 148, 159 and secure them to the frame 124.

The dual torsion spring 204 comprises a U-shaped spring end 208 extending from the coils 206. The U-shaped spring end 208 is located beneath the lever portion 152 of the cam 130 to bias upwardly against the lever portion 152 of the cam 130. Sides 210 of the U-shaped spring end 208 run along an inside surface of the side walls 136, 138 of the frame 124, making it less likely for external interference with operation of the dual torsion spring 204. Bent tangs 212 of the dual torsion spring 204 fit into holes 213 formed in the side walls 136, 138 of the frame 124.

Figure 24:
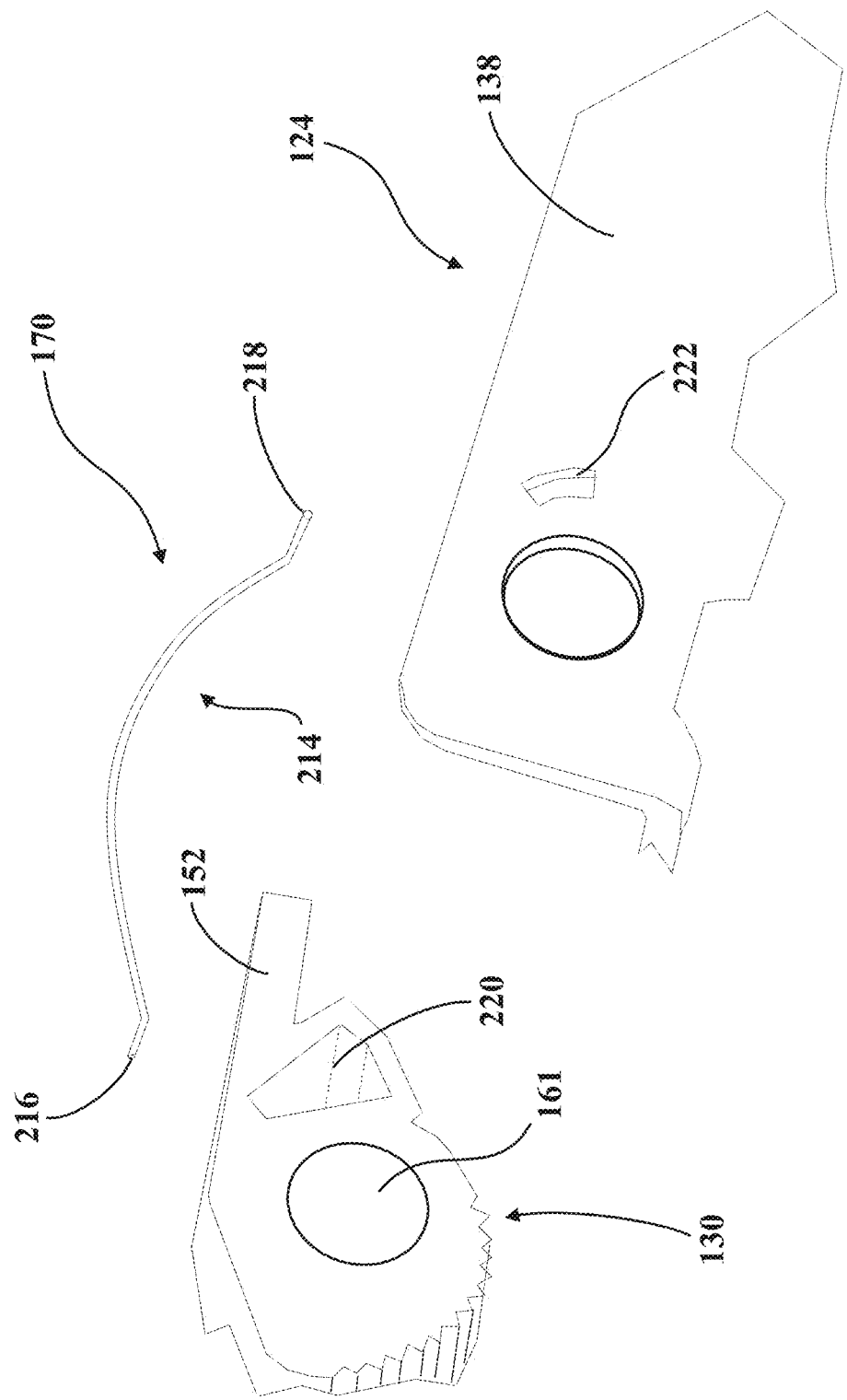
FIG. 24 is a partial exploded perspective view illustrating another biasing device for the cam.

FIG. 24 illustrates another example of the biasing device 170 that could be employed to bias the cam 130 toward the plurality of clamping positions. In this example, the biasing device 170 comprises a spring 214 having an arc shape and opposing spring ends 216, 218. In this example, the cam 130 defines a spring through hole 220 to receive the spring 214 such that the ends 216, 218 of the spring 214 extend from the cam 130 on opposing sides of the cam 130 to engage the frame 124. In particular, slots 222 (only one shown) are incorporated into the side walls 136, 138 of the frame 124 to receive the spring ends 216, 218. Thus, the cam 130 substantially encloses the spring 214 to limit the potential for external interference with its function. During normal operation, prior to the lever portion 152 being actuated by the user, a top of the arc of the spring 214 presses against the cam 130 at a top of the spring through hole 220. At the same time, the spring ends 216, 218 press against a bottom surface of the slots 222 to urge the lever portion 152 of the cam 130 upwardly. Thus, the lever portion 152 is biased upwardly and the cam 130 is biased toward the plurality of clamping positions. When the lever portion 152 is actuated by the user, the spring 214 is compressed by virtue of the arc of the spring 214 being pressed downwardly, while the spring ends 216, 218 remain pressed against the bottom surface of the slots 222. When the harness assembly 102-114 is under high tension loads, the lever portion 152 of the cam 130 and the spring 214 rotate upwardly. The slots 222 allow the spring ends 216, 218 to move freely upward if necessary (depending on how far the cam 130 rotates under the high tension loads). Moreover, the angular geometry of the spring through hole 220 (e.g., spaced apart, diverging, flat side surfaces) are such that the spring 214 is able to deform freely in the spring through hole 220 and still allow the cam 130 to rotate. The spring 214 is symmetrical between the spring ends 216, 218 and the spring through hole 220 is uniformly formed through the cam 130 so that the biasing force provided by the spring 214 is applied symmetrically to the cam 130. Furthermore, since the spring through hole 220 is separate from the through hole 161 in the cam 130 that receives the pin 155, the spring through hole 220 does not compromise the balance of loads on the flexible restraint 120. It should be appreciated that the through hole 161 and/or the spring through hole 220 could be formed via injection molding, by machining, or the like.

Figure 25:
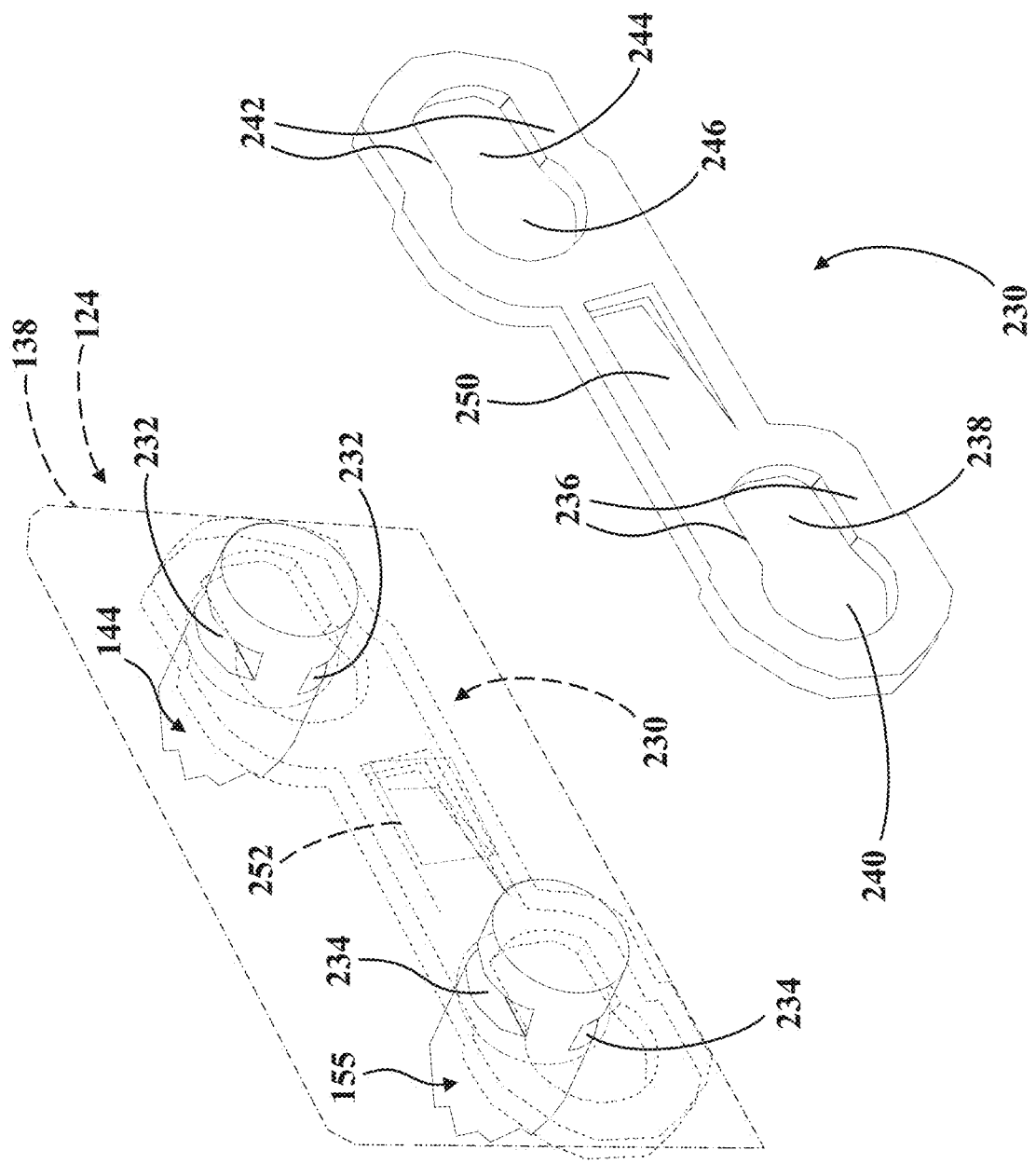
FIG. 25 is a partial exploded perspective view illustrating a retainer plate for pins of the adjuster.

Referring to FIG. 25, a retainer plate 230 may be used to secure the pins 144, 155 to the frame 124 (see hidden lines showing retainer plate 230 in final position). In this example, each of the pins 144, 155 define keyways 232, 234. The retainer plate 230 is shaped to engage the pins 144, 155 via the keyways 232, 234. In particular, the retainer plate 230 has first keys 236 defining a first slot 238 that extends into a first opening 240 and second keys 242 defining a second slot 244 that extends into a second opening 246. The keys 236, 242 are shaped to fit in the keyways 232, 234 of the pins 144, 155. The retainer plate 230 also has a locking detent 250 to engage the frame 124 via a detent pocket 252 and hold the retainer plate 230 in position relative to the pins 144, 155. During assembly, the pins 144, 155 are placed into their corresponding openings in the side walls 136, 138 such that the distal ends of the pins 144, 155 protrude through one of the side walls 136, 138 exposing the keyways 232, 234 externally. The openings 240, 246 of the retainer plate 230 are then aligned with the pins 144, 155 and fitted over the pins 144, 155 until the keys 236, 242 align with the keyways 232, 234. Once the keys/keyways are aligned, then the retainer plate 230 is moved to place the keys 236, 242 in the keyways 232, 234. Once the keys 236, 242 move far enough into the keyways 232, 234 to suitably secure the pins 144, 155 to the frame 124, the locking detent 250 springs into the detent pocket 252 to hold the retainer plate 230 is position relative to the frame 124. Other locking features may be employed to hold the retainer plate 230 in position relative to the frame 124. In the version shown, the keys 236, 242 and keyways 232, 234 have a mating, double D cross-sectional shape to limit/prevent rotation of the pins 144, 155. Thus, the retainer plate 230 is able to hold multiple pins 144, 155, while also preventing rotation of the pins 144, 155. Other mating configurations (e.g., geometries) to secure the retainer plate 230 onto the pins 144, 155 are also contemplated.

Figure 27:
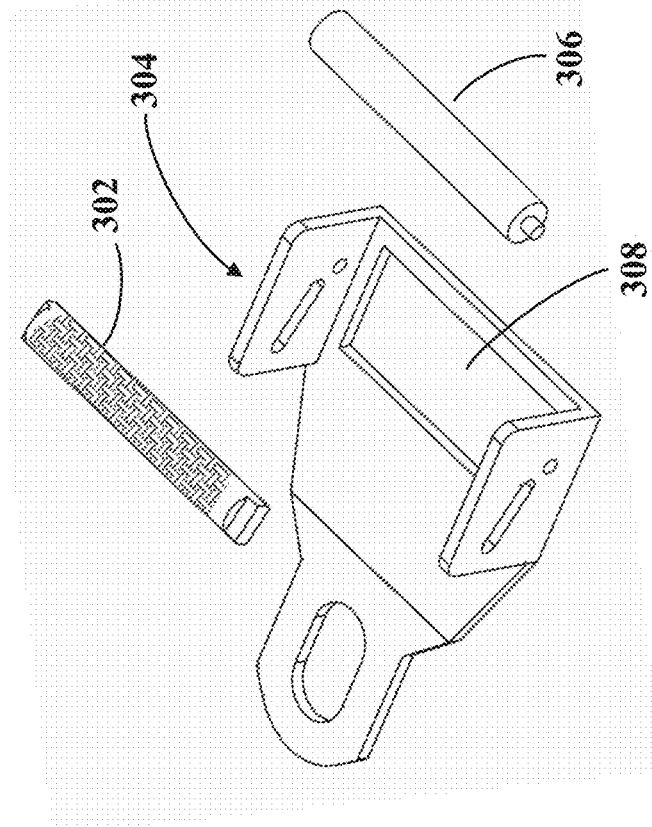
FIG. 27 is an exploded perspective view of the adjuster of FIG. 26.
Figure 26:
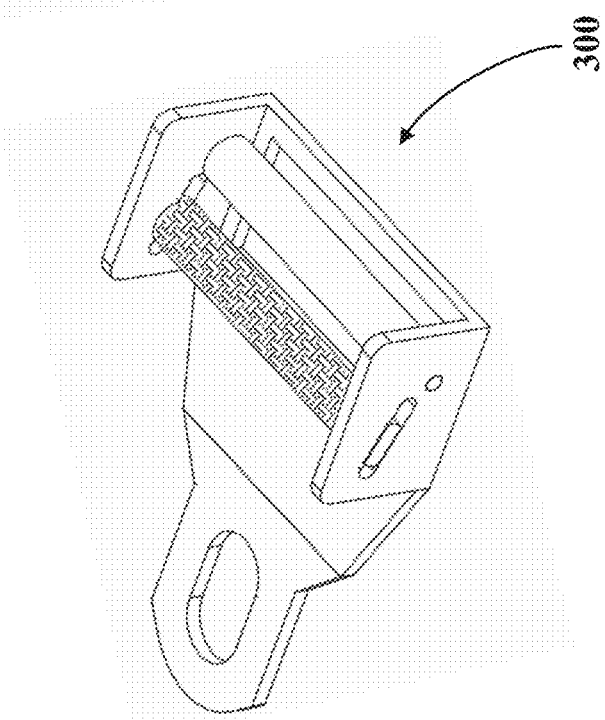
FIG. 26 is a top perspective view of another adjuster.
Figure 28:
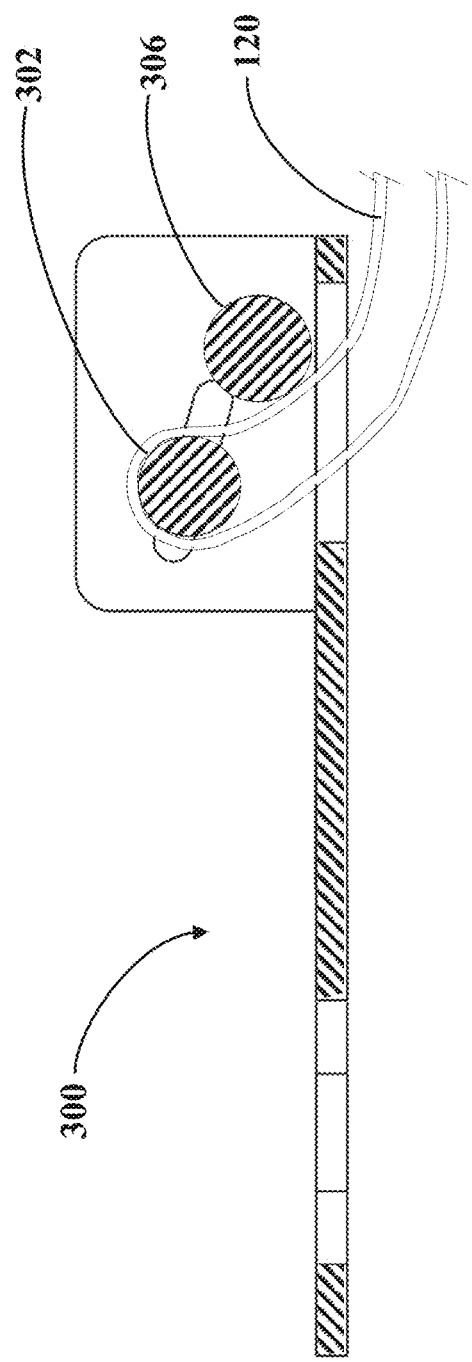
FIG. 28 is a cross-sectional view of the adjuster of FIG. 26 illustrating a knurled bar and roller.

Referring to FIGS. 26-28, another adjuster 300 is shown. In this version of the adjuster, a knurled bar 302 slides relative to a frame 304 during operation. The coating on the coated fabric of the flexible restraint 120 may become tacky when cleaned with certain chemicals. Accordingly, in this version, a roller 306, much like the roller 142, is provided near an edge of an opening 308 in the frame 304. The roller 306 is positioned to reduce or eliminate contact of the flexible restraint 120 with the frame 304, and provide rolling friction, to ease adjustment. The roller 306 can also be positioned to allow contact between the flexible restraint 120 and the frame 304 during adjustment, but while minimizing or reducing the angle of contact between the flexible restraint 120 and the frame 304 to reduce friction.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An adjuster for use with a flexible restraint, the adjuster comprising:
   a frame defining an opening and having a clamping surface;
   a restraint guide comprising a roller arranged for frictional engagement with the flexible restraint, the roller being rotatably supported by a pin coupled to the frame and positioned relative to the opening so that the flexible restraint is capable of being routed over the clamping surface, wrapped about the roller, and passed through the opening; and
   a cam rotatably coupled to the frame about a rotational axis and comprising a lever portion arranged to be actuated by a user and a clamping portion arranged to clamp the flexible restraint against the clamping surface, the cam being rotatable to a plurality of clamping positions,
   wherein the clamping portion defines a cam profile in cross-section that has a spiral shape, the cam profile having clamping points, each of the clamping points defined as a nearest point on the cam profile to the clamping surface at each of the plurality of clamping positions,
   wherein the cam defines a fixed plane passing through the rotational axis normal to the clamping surface, and the cam defines a clamping plane parallel to the clamping surface passing through each of the clamping points, wherein each of the clamping points are offset from the fixed plane by a first distance and the clamping plane is offset from the rotational axis by a second distance, with a ratio of the second distance to the first distance being in a range of from 2.5 to 5.5 for each of the clamping positions.

2. The adjuster of claim 1, wherein the ratio of the second distance to the first distance is in a range of from 3.0 to 4.0 for each of the clamping positions.

3. The adjuster of claim 2, wherein the first distance is from 0.05 inches to 0.1 inches and the second distance is from 0.15 inches to 0.4 inches.

4. The adjuster of claim 1, wherein the clamping portion has teeth extending to tips that define the cam profile and each of the teeth has a generally triangular shape and is symmetrical about a midline disposed normal to the cam profile.

5. The adjuster of claim 1, wherein the roller comprises a plurality of rolling segments each rotatably supported by the pin.

6. The adjuster of claim 1, wherein the frame comprises a brake configured to be spaced from the roller in normal operation and to contact the roller upon bending of the restraint guide to brake rotation of the roller.

7. The adjuster of claim 6, wherein the frame comprises a wall and the brake comprises a flanged portion of the wall.

8. The adjuster of claim 1, comprising a biasing device arranged to act between the frame and the cam to bias the cam toward the plurality of clamping positions.

9. The adjuster of claim 8, comprising a spring-supporting pin coupled to the frame, wherein the biasing device comprises a dual spring having coils disposed about the spring-supporting pin and a U-shaped spring end located to bias against the lever portion of the cam.

10. The adjuster of claim 8, wherein the biasing device comprises a spring having opposing ends and the cam defines a spring through hole to receive the spring such that the ends of the spring extend from the cam on opposing sides of the cam to engage the frame.

11. The adjuster of claim 8, wherein the biasing device comprises a spring and the cam has a first side with a first pocket to receive the spring and the cam has a second side, opposite the first side, the second side having a second pocket.

12. The adjuster of claim 11, comprising a stop coupled to the frame, wherein the stop extends into the second pocket, the cam having an abutment arranged to engage the stop upon rotation of the cam by the user from one of the clamping positions to a releasing position.

13. The adjuster of claim 12, comprising a pin supporting rotation of the cam, wherein the frame comprises a first wall and a side wall extending from the first wall, the stop comprising a collar disposed about the pin and a protrusion extending from the collar, through the side wall, and into the second pocket.

14. The adjuster of claim 13, wherein the pin has a head and a shaft extending from the head and the collar defines an opening for receiving the head, the head and opening shaped to prevent relative rotation between the pin and the collar.

15. An adjuster for use with a flexible restraint, the adjuster comprising:
   a frame defining an opening and having a clamping surface;

a cam rotatably coupled to the frame and comprising a lever portion arranged to be actuated by a user and a clamping portion arranged to clamp the flexible restraint against the clamping surface; and a restraint guide comprising a roller rotatably coupled to the frame and positioned relative to the opening so that the flexible restraint is capable of being routed over the clamping surface, wrapped about the roller, and passed through the opening, wherein the frame comprises a brake configured to be spaced from the roller in normal operation and to contact the roller upon bending of the restraint guide to brake rotation of the roller.

16. The adjuster of claim 15, wherein the frame comprises a wall and the brake comprises a flanged portion of the wall.

17. An adjuster for use with a flexible restraint, the adjuster comprising:
- a frame defining an opening and having a clamping surface;
- a restraint guide coupled to the frame and positioned relative to the opening so that the flexible restraint is capable of being routed over the clamping surface, wrapped about the restraint guide, and passed through the opening;
- a cam rotatably coupled to the frame and comprising a lever portion arranged to be actuated by a user and a clamping portion arranged to clamp the flexible restraint against the clamping surface, the cam being rotatable to a plurality of clamping positions;
- a biasing device arranged to act between the frame and the cam to bias the cam toward the plurality of clamping positions; and
- a stop coupled to the frame and arranged to engage the cam upon rotation of the cam by the user from one of the clamping positions to a releasing position.

18. The adjuster of claim 17, comprising a pin supporting rotation of the cam, wherein the frame comprises a first wall and a side wall extending from the first wall, the stop comprising a collar disposed about the pin and a protrusion extending from the collar, through the side wall.

19. The adjuster of claim 18, wherein the pin has a head and a shaft extending from the head and the collar defines an opening for receiving the head, the head and opening shaped to prevent relative rotation between the pin and the collar.

20. The adjuster of claim 18, wherein the cam defines a pocket receiving the stop and an abutment for engaging the stop upon rotation of the cam to the releasing position, the pocket sized to allow the stop to travel in the pocket as the cam moves to the plurality of clamping positions.

\* \* \* \* \*